US011835490B2

(12) United States Patent
Tey

(10) Patent No.: US 11,835,490 B2
(45) Date of Patent: Dec. 5, 2023

(54) DEVICE AND METHOD FOR DETECTING GROUT COMPACTNESS OF SPLICE SLEEVE

(71) Applicant: ZHEJIANG UNIVERSITY, Zhejiang (CN)

(72) Inventor: MingWang Tey, Zhejiang (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 243 days.

(21) Appl. No.: 17/233,481

(22) Filed: Apr. 17, 2021

(65) Prior Publication Data
US 2021/0293676 A1     Sep. 23, 2021

Related U.S. Application Data

(63) Continuation of application No. PCT/CN2019/128227, filed on Dec. 25, 2019.

(30) Foreign Application Priority Data

Dec. 25, 2018   (CN) .......................... 201811592823.2

(51) Int. Cl.
  *G01N 33/38* (2006.01)
  *G01N 3/30* (2006.01)
  (Continued)

(52) U.S. Cl.
  CPC .............. *G01N 3/066* (2013.01); *G01N 3/30* (2013.01); *G01N 33/383* (2013.01);
  (Continued)

(58) Field of Classification Search
  CPC ... G01N 2203/0005; G01N 2203/0007; G01N 2203/0008; G01N 2003/001;
  (Continued)

(56) References Cited

U.S. PATENT DOCUMENTS

2015/0097589 A1     4/2015   Orazem et al.

FOREIGN PATENT DOCUMENTS

CN        106501495 A  *  3/2017
CN        106596298 A  *  4/2017
(Continued)

*Primary Examiner* — Herbert K Roberts
(74) *Attorney, Agent, or Firm* — Idea Intellectual Limited; Margaret A. Burke; Sam T. Yip

(57) ABSTRACT

The invention relates to a device and method for detecting the grout compactness of splice sleeve, the device comprising a preloading member, a force transmission rod, a telescopic adjustment member, a vibration sensor and a data acquisition system. The rigid preloading member is used to fix the force transmission rod to the wall where the connecting structure of the splice sleeve is located, so that the end of the force transmission rod can be securely fastened to a rebar surface of a splice sleeve to be detected; the vibration sensor is fixed to the force transmission rod; the data acquisition system is used to acquire vibration signals from the vibration sensor. The grout compactness of splice sleeve is quantitatively analyzed, and a time-domain and frequency-domain signal may be used to obtain a peak-to-width ratio $R_{Npw}$ and a peak frequency $\Omega_{Peak}$ signal to serve as a standard for the quantitative analysis.

32 Claims, 9 Drawing Sheets

(51) Int. Cl.
  *G01N 3/06* (2006.01)
  *G01N 29/04* (2006.01)
(52) U.S. Cl.
  CPC ..... *G01N 29/045* (2013.01); *G01N 2203/001* (2013.01); *G01N 2203/0039* (2013.01); *G01N 2203/0058* (2013.01)
(58) Field of Classification Search
  CPC .... G01N 29/045; G01N 33/38; G01N 33/383; E02D 5/74; E04C 5/162; E04C 5/163; E04C 5/165; E04C 5/166; E04C 5/167
  See application file for complete search history.

(56) References Cited

FOREIGN PATENT DOCUMENTS

| | | | |
|---|---|---|---|
| CN | 106596298 A | | 4/2017 |
| CN | 107328921 A | * | 11/2017 |
| CN | 107328921 A | | 11/2017 |
| CN | 107389791 A | * | 11/2017 |
| CN | 107478719 A | * | 12/2017 |
| CN | 107478719 A | | 12/2017 |
| CN | 108051480 A | * | 5/2018 |
| CN | 108761049 A | * | 11/2018 |
| CN | 108802188 A | * | 11/2018 |
| CN | 108827825 A | * | 11/2018 |
| CN | 108828197 A | * | 11/2018 |
| CN | 108872548 A | * | 11/2018 |
| CN | 108956962 A | * | 12/2018 |
| CN | 109406340 A | | 3/2019 |
| JP | WO2012133784 A1 | * | 7/2014 |

\* cited by examiner

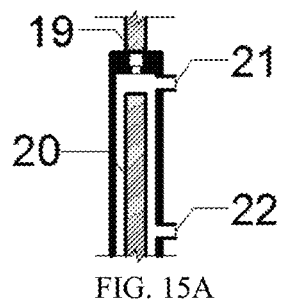
FIG. 15A
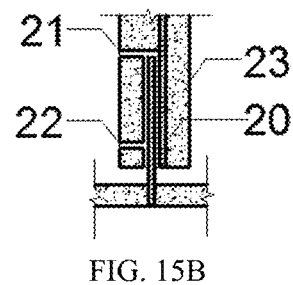
FIG. 15B
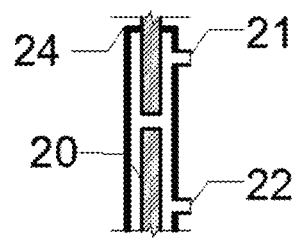
FIG. 15C
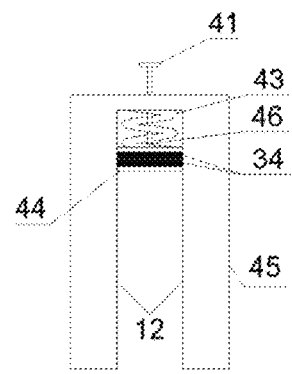
FIG. 16
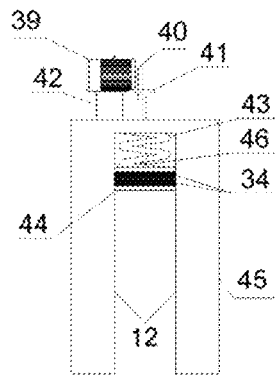
FIG. 17
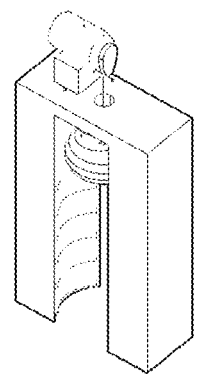
FIG. 18
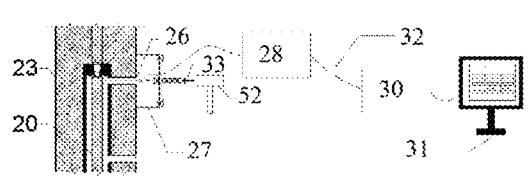
FIG. 19A
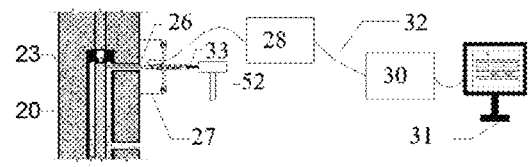
FIG. 19B
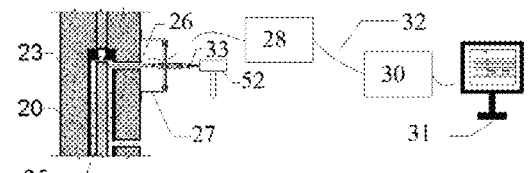
FIG. 19C
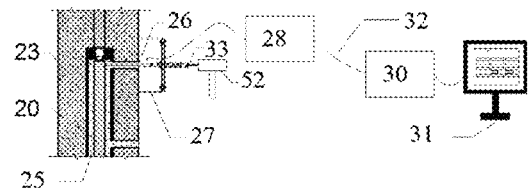
FIG. 19D
FIG. 19

DEVICE AND METHOD FOR DETECTING GROUT COMPACTNESS OF SPLICE SLEEVE

CROSS-REFERENCE TO RELATED APPLICATIONS

This application is a continuation of International Patent Application No. PCT/CN2019/128227, filed on Dec. 25, 2019, which claims the benefit of priority from Chinese Patent Application No. 201811592823.2, filed on Dec. 25, 2018. The content of the aforementioned applications, including any intervening amendments thereto, is incorporated herein by reference in its entirety.

FIELD

This invention belongs to the field of measurement, and in particular relates to the device and method for detecting the grout compactness of splice sleeve in construction engineering.

BACKGROUND

Prefabricated building structure is a green, environment-friendly, and energy-saving building method, and has attracted widespread attention from relevant personnel worldwide for its many advantages, as it represents a rapid technical progress in the construction industry. The quality control of prefabrication is very important to ensure the safety of the prefabricated construction works, but it still lacks effective engineering testing, detection, evaluation and measurement methods, as such, it is imperative to embark on intensive research and development activities to address the above shortcomings, to fast-track the application and implementation of this new construction technology post quality control stages.

The prefabricated building structure is generally composed of several prefabricated components connected together using the grouted splice sleeve, and if these connections encountered anything problems which remain unresolved, large safety accidents will eventually occur, often with disastrous consequences. The quality of the splice sleeve depends on whether the grouting is full and compact. Therefore, a robust and reliable quantitative detection method to determine the grout compactness of the splice sleeves is required to test for the integrity and quality of the sleeves' key connections in a prefabricated structure, to ensure safety.

At present, based on existing literature and patents, there are several methods used to test for the grout compactness of splice sleeve. Among some the main methods currently employed include the Electric Resistance Test Method, Embedded Steel Wire Drawing Method, Vibration Sensor with Damped Method, Impact Echo-Test (IET) and Ultrasonic Pulse-Echo Test (UPET).

There are some drawbacks using the Electric Resistance Test Method, Embedded Steel Wire Drawing Method, and Vibration Sensor with Damped Method, as the sensors and measurement kits used to be embedded prior to grouting, before the actual detection and measurement can be performed. This prohibits random testing from being executed, as only those points embedded with these items can be sampled and tested. Moreover, such embeddings may have been damaged during or post grouting and hence can no longer be tested. Secondly, since the sensors and kits need to be embedded, it is impossible to conduct a large number of tests due to cost constraints, and this poses some reliability concerns.

To overcome the above problems, the dynamic test method is the most widely used, with IET being the leading method, followed by UPET. The basic principle of the IET method is to use the reflected waves' characteristics propagated through vibration, to determine the exact locations and range of defects, and to analyze the grout compactness of splice sleeve. But similarly, since the distance between the incident surface and the reflection surface is small, the incident waves and the reflected waves are often superimposed, resulting in insignificant undulation effects, and therefore the location and the degree of defectivity cannot be directly identified.

For the UPET method, it also needs to exert an ultrasonic oscillation on the sleeve to be tested, and the incident wave and reflected wave (or transmitted wave) collected by the ultrasonic sensor are analyzed to determine the potential of the grouted bodies' defects. The size of defects between the sleeve and the rebar are much smaller than the wavelength of the ultrasonic wave. This method is unable to produce a high resolution of the defect, as such the defect often goes undetected.

Therefore, at present, there is no effective engineering solution available for the detection for the grout compactness of splice sleeve. Against this background, this patent proposes a new method, that is, to apply a certain preload to the rebar via the force transmission rod of a special device, and then apply a force at the end of the force transmission rod (may use hammering method). Due to the preload exerted by the force transmission rod, the vibration of the rebar after getting a pulse, can then be transmitted to the force transmission rod. The vibration signal from the lateral vibration of the rebar can be acquired with the aid of the strain gauge installed on the force transmission rod. The grout compactness of splice sleeve connector can be analyzed by analyzing the time-domain and frequency-domain signals from the acquired vibration signals.

SUMMARY

The purpose of this invention is to resolve the problems mentioned above and to provide a device and method for detecting the grout compactness of splice sleeve connector.

The specific technicalities adopted by this invention are as follows:

Firstly, this invention provides a device for detecting grout compactness of splice sleeve, which include a rigid preloading member, a force transmission rod, a telescopic adjustment member, a vibration sensor, and a data acquisition system;

The force transmission rod is a rigid rod body installed on a rigid preloading member using the telescopic adjustment member. This rigid preloading member is used to fix the force transmission rod to the wall where the connecting structure of the splice sleeve is located, and the telescopic adjustment member is fixed to the rigid preloading member and used to control the movement of the force transmission rod along a direction in perpendicular to the wall, so that the end of the force transmission rod can be securely fastened to a rebar surface for better detection. The vibration sensor is fixed to the force transmission rod, and the data acquisition system is used to acquire vibration signals from the vibration sensor.

Secondly, this invention provides a method for detecting grout compactness of splice sleeve. The devices and tools used in this method include a preloading member, a nut, a force transmission rod, a hammer and a vibration sensor. The preloading member is cover-shaped, hollow and rigid member, and its bottom is fixed around the wall where the splice sleeve to be tested is located; the preloading member is provided with a through hole, and a nut is fixed at the position of the through hole; the force transmission rod is a rigid body rod, with its middle part male threaded, the force transmission rod passes through the through hole on the preloading member cover and is screwed into the nut; the thread and nut drive the force transmission rod to move up and down; the end of the force transmission rod is securely fastened to the grouted body of the splice sleeve to be detected; the vibration sensor is fixed to the force transmission rod; the hammer is used to exert a force to the end of the force transmission rod;

The steps involved in the detection are as follows:

Step 1: When testing the grout compactness of splice sleeve, the force transmission rod with the vibration sensor is extended into the wall body at the position of the grouting extraction hole or the grouting hole on the sleeve's outer wall, to make the end of the force transmission rod securely fastened to the grouted body, then fixing the bottom of the preloading member to the wall surface.

Step 2: Rotate and tighten the force transmission rod through the nut fixed inside the device, so that the end of the force transmission rod is securely fastened to the grouted body of the splice sleeve to be tested, to ensure that the force transmission rod and grouted body will not be separated during the test.

Step 3: Exert a force to the end of the force transmission rod with a hammer, and capture the variation curve of the vibration signal over time through the data acquisition system connected to the vibration sensor.

Step 4: An indoor full-scale model test can now be carried out, by setting up several groups with different grout compactness gradient for comparative test; under the same hammering force condition as in Step 3, use the same dynamic detection device to obtain the variation curve on the vibration signals of different grout compactness over time, and compare these with the variation curve of the vibration signal measured in Step 3, to determine the actual distribution interval of grout compactness, and the quantitative judgment of the grout compactness of the splice sleeve is completed.

Thirdly, this invention provides a method for detecting grout compactness of splice sleeve, which include the following steps:

S1: The rigid force transmission rod is securely fastened to the rebar surface extended into the grouting extraction hole on the sleeve to be tested, and maintain a prestress between each other; the vibration sensor is fixed to the force transmission rod, which can synchronize vibration with the force transmission rod to acquire data; the vibration sensor mentioned above can consists of one or more combinations of a strain gauge, a displacement transducer, an accelerometer and a velocity transducer.

S2: Exert a force along the axial direction of the force transmission rod to the rebar inside the sleeve structure, to make the rebar and the force transmission rod vibrate synchronously, and capture the vibration signal from the force transmission rod due to pulse via the vibration sensor.

S3: Obtain some parametric values from the vibration signal's key indicators, which may consist of one or more combinations of time-domain or frequency-domain indicators.

The time-domain indicators include: the amplitude of the N th half-wave in the waveform obtained from the time-domain vibration signal, the any width at any amplitude $\Delta t_{Nwidth}$, and the peak-to-width ratio $R_{Npw}$ at any width at any amplitude $\Delta t_{Nwidth}$, N=1 or 2;

The frequency-domain indicators include: the peak frequency which corresponds to the maximum amplitude obtained from the frequency-domain vibration signal.

S4: Based on the parametric values obtained in S3, and the distribution interval of the time-domain or frequency-domain indicators which corresponds to the compactness of different grouted bodies, the grout compactness of the splice sleeve is thus determined.

Fourthly, this invention provides a method for detecting grout compactness of splice sleeve using the detection devices highlighted earlier, which include the following steps:

S1: Install the rigid preloading member on the wall where the splice sleeve to be tested is located, fix the force transmission rod to the wall via the telescopic adjustment member; ensure the end of the force transmission rod is securely fastened to the surface of the rebar in the sleeve, and maintain a prestress between each other.

S2: Exert a force along the axial direction of the force transmission rod, to make the rebar and the force transmission rod vibrate synchronously, and capture the original electrical signal detected by the vibration sensor due to pulse; the original electrical signal is amplified by a small-signal/low-noise amplifier and a filter to eliminate the noise; and the electrical signal is then sampled and converted into a digital signal by an analog-to-digital converter and stored in the data acquisition system;

S3: Wiener filtering is applied to the amplified electrical signal stored in the data acquisition system to enhance the target frequency;

S4: The Wiener filtered electrical signal is then inputted into the Kalman filter, and further filtering is performed according to steps S41 to S46 below, wherein:

S41: For the $i^{th}$ sampling point in the amplified electrical signal, $x_i$, a filter window of size, $N_{fw}$ is set with the $i^{th}$ sampling point as the center, and obtained a vector $Data_i$ by composing all the sampling points in the filter window; the predicted state estimate of electrical signal values are $$\hat{Amp}^- = \text{D\"ata} = \frac{1}{N}\sum_{j=1}^{N_{fw}} Data_i^j;$$

wherein the Däta is the average of all sampling points in the current filter window, $Data_i^j$ represents the signal value of the $j^{th}$ sampling point in the vector $Data_i$, $j \in [1, N_{fw}]$.

S42: Covariance matrix of the observation noise $$R = \frac{1}{N-1}\sum_{j=1}^{N_{fw}} |Data_i^j - \text{D\"ata}|^2;$$

S43: Calculate optimal Kalman gain $$K = \frac{|\hat{A}mp^-| \cdot H^T}{H \cdot |\hat{A}mp^-| \cdot H^T + R};$$

wherein the H is the observation matrix, T means transpose;

S44: Calculate the amplitude of the electrical signal output after filtering at the $i^{th}$ sampling point:

$$\hat{A}mp = \begin{cases} -\{|\hat{A}mp^-| + K \cdot (|Data_{x_i}| - H \cdot |\hat{A}mp^-|)\}, & \hat{A}mp^- < 0 \text{ and } Data_{x_i} < 0 \\ |\hat{A}mp^-| + K \cdot (Data_{x_i} - H \cdot \hat{A}mp^-), & \text{others} \end{cases}$$

In the formula: $Data_{x_i}$ represents the sampling value of the $i^{th}$ sampling point $x_i$;

S45: Before filtering the next sampling point, update the predicted state estimate of electrical signal value $\hat{A}mp^-$ = $(1-K \cdot H) \cdot D\ddot{a}ta + Q$, where Q is the state transition covariance matrix; meanwhile, i=i+1.

S46: Repeat steps S42 to S45 for the remaining sampling points in the amplified electrical signals in sequence to complete Kalman filtering;

S5: Digital filtering the Kalman-filtered signals. The process is to input the signal into a band-stop filter to suppress the frequency of the powerline interference, and then filter out the high frequency through a low-pass filter at 3000 Hz, and derive a new time-domain data.

S6: The amplitude of the $N^{th}$ half-wave in the waveform obtained from the time-domain vibration signal; the any width at any amplitude $\Delta t_{Nwidth}$, and the peak-to-width ratio $R_{Npw}$ at any width at any amplitude $\Delta t_{Nwidth}$; wherein N=1 or 2.

S7: Perform Fast Fourier Transform (FFT) on the new time-domain data to obtain the FFT power spectrum, and extract the frequency and amplitude from the power spectrum, and obtain the peak frequency; the peak frequency is a frequency corresponding to the maximum power amplitude in the frequency-domain.

S8: Taking any one or more of the peak amplitude $A_{Npeak}$, the pulse width $\Delta t_{Nwidth}$, the peak-to-width ratio $R_{Npw}$, and the peak frequency $\Omega_{Peak}$ as the indicators' characteristics. According to the parametric values obtained from S6 to S7, based on the distribution interval of these parametric values which correspond to the compactness of different grouted bodies, determine the grout compactness of the splice sleeve to be tested.

Compared with prior technology, the present invention has the following benefits:

1. The device and method for detecting grout compactness of splice sleeve of the present invention can be used for qualitative and quantitative determination when the grouting is completed, and conduct sampling inspections and repeatability tests on the quality of different splice sleeve; the device can be reused after the test is completed, which offer great practical value for the quality inspection of field connection joints in construction projects.
2. The present invention provides a new type of detachable detection device, which separates the rigid preloading member from the force transmission rod, the rigid preloading member is separately positioned and installed, and the force transmission rod is detachable through the preload applying plate, assembled on the rigid preloading member, and directly disassembled after use. The rigid preloading member can be used as required, and more people can divide the work, which improves the efficiency of the entire testing.
3. In the new detachable detection device, because the combination of the preload applying plate and the lock are used to exert prestress to the force transmission rod, it is far easier to control the prestress magnitude than to simply adjust the force transmission rod; since there is no torque caused by twisting, it is not easy to make the rigid preloading member fall off.
4. In the present invention, for the quantitative detection of the grout compactness of splice sleeve, a plurality of the indicators' characteristics obtained from the signal's curve are optimized, which further simplifies the comparison of the signal's curve and facilitates the automation of the method.
5. In the present invention, a variety of vibration sensors can be used in combination. Compared with a single sensor using only a strain gauge, the present invention can compare and verify the results obtained from different sensors.

BRIEF DESCRIPTIONS OF THE DRAWINGS

FIG. 15 shows three types of splice sleeves' structures: FIG. 15A illustrates a half-grout sleeve; FIG. 15B illustrates a rebar anchoring grouting structure; and FIG. 15C illustrates a full-grout sleeve.

FIG. 16 is a schematic view of a structure of a manual impact hammer.

FIG. 17 is a schematic view of a structure of an auto impact hammer.

FIG. 18 is a 3D schematic view of a structure of an auto impact hammer.

FIG. 19 is a schematic view of a device detection status under 4 types of different grout compactness of splice sleeves; FIG. 19A illustrates when the inner cavity of the sleeve is grout-free; FIG. 19B illustrates when the inner cavity of the sleeve is ⅓ grouted;

FIG. 19C illustrates when the inner cavity of the sleeve is ⅔ grouted; and FIG. 19 D illustrates when the inner cavity of the sleeve is fully grouted.

Figure 20:
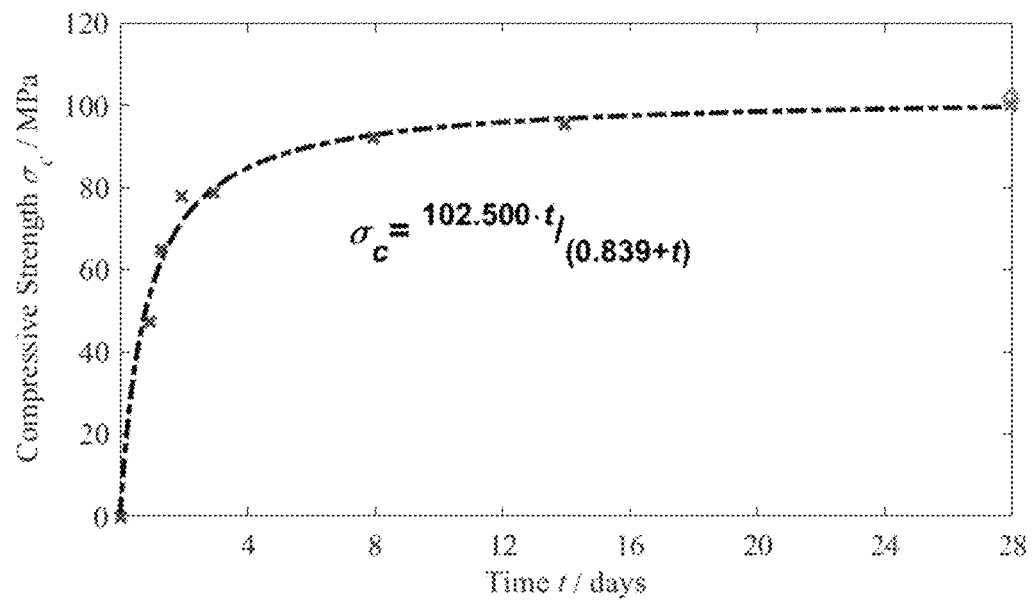

FIG. 20 is the compressive strength $\sigma_c$ of the specimen at different times after grouting; where, ------ is a fitting line, × is the test result under the same curing condition, ◇ is the test result under steam curing.

Figure 21A:
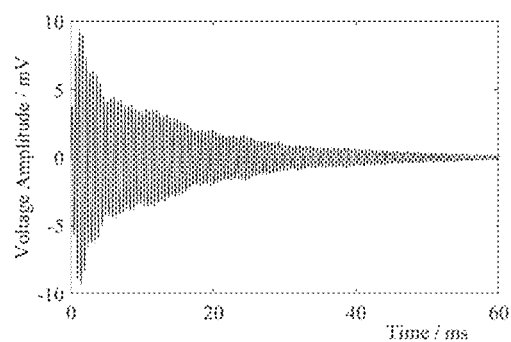
Figure 21B:
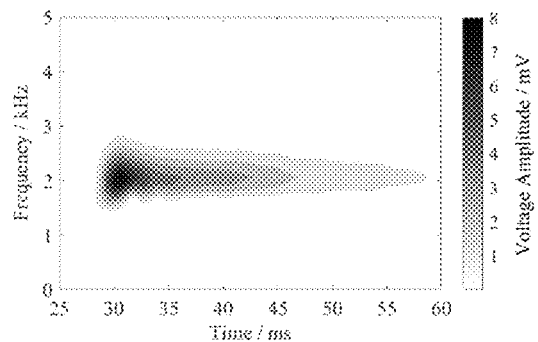
Figure 21C:
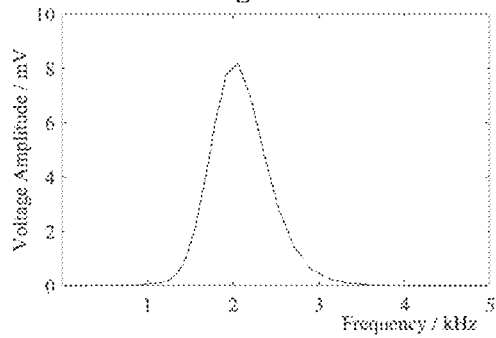

FIG. 21A-21C are the results from the detection signal for the free-grouted sleeve model; where FIG. 21A, FIG. 21B and FIG. 21C are the diagrams depicting the time-domain, Wavelet power spectrum, and the frequency-domain, respectively.

Figure 22A:
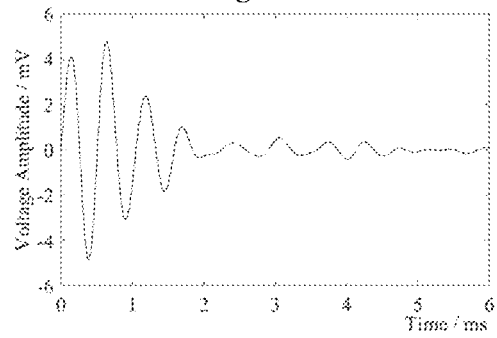
Figure 22B:
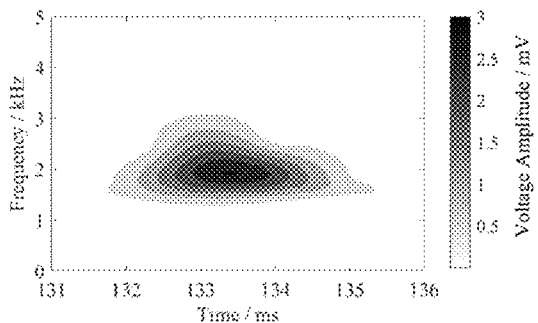
Figure 22C:
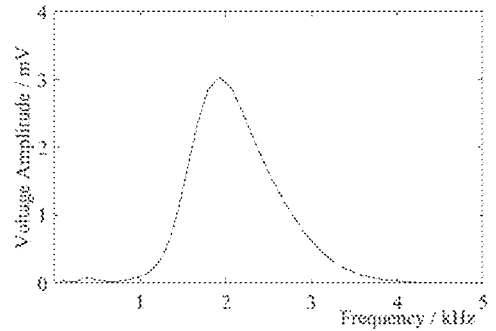

FIG. 22A-22C are the results from the detection signal for the ⅓ grouted sleeve model; where FIG. 22A, FIG. 22B and FIG. 22C are the diagrams depicting the time-domain, Wavelet power spectrum, and the frequency-domain, respectively.

Figure 23A:
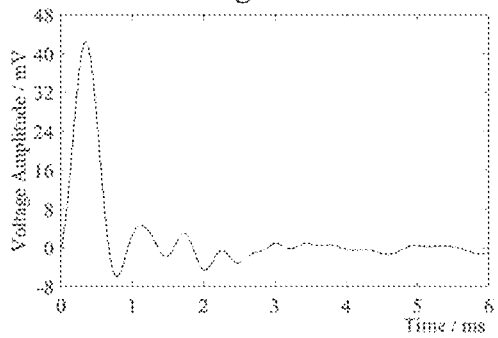
Figure 23B:
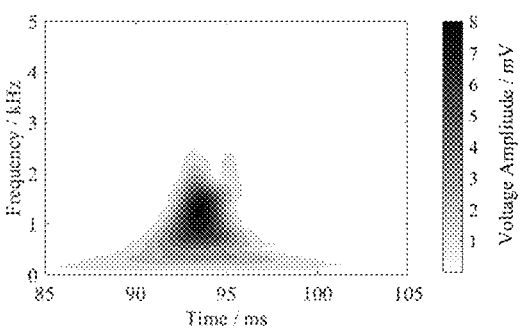
Figure 23C:
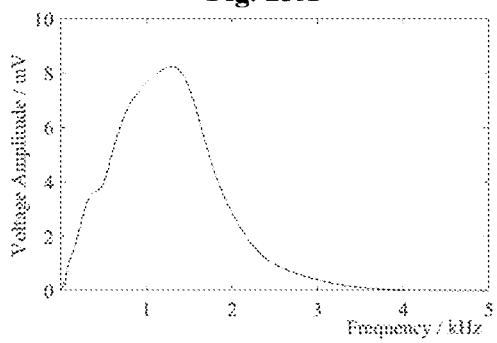

FIG. 23A-23C are the results from the detection signal for the ⅔ grouted sleeve model; where FIG. 23A, FIG. 23B and FIG. 23C are the diagrams depicting the time-domain, Wavelet power spectrum, and the frequency-domain, respectively.

Figure 24A:
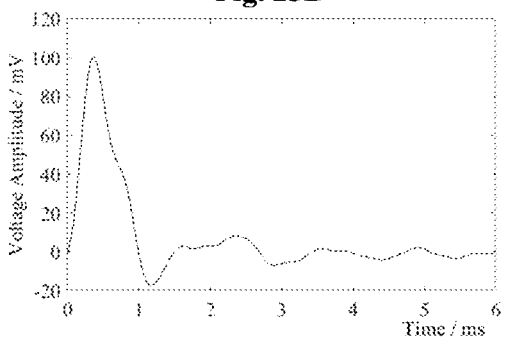
Figure 24B:
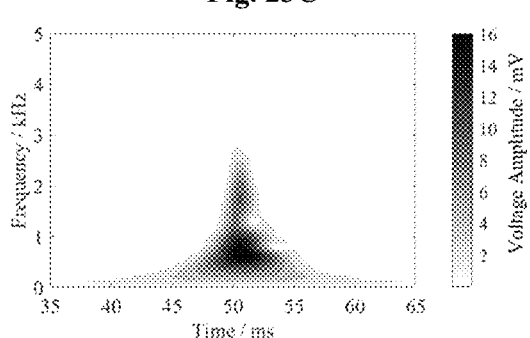
Figure 24C:
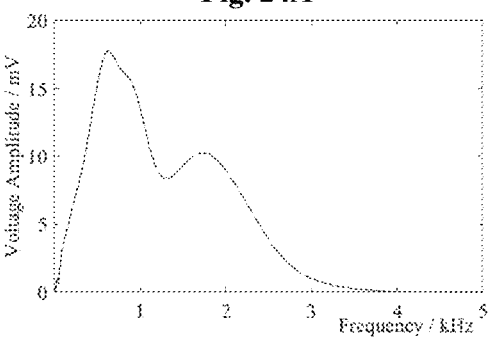

FIG. 24A-24C are the results from the detection signal for the full-grouted sleeve model; where FIG. 24A, FIG. 24B and FIG. 24C are the diagrams depicting the time-domain, Wavelet power spectrum, and the frequency-domain, respectively.

Figure 25:
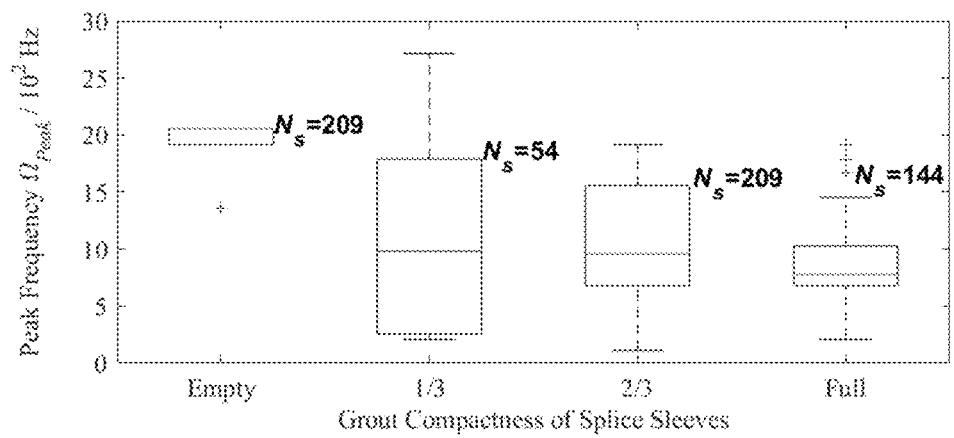

FIG. 25 is the statistical distribution depicting the peak frequency value $\Omega_{Peak}$ which corresponds to different grouted compactness after the grouted bodies were cured for 24 hours; $N_s$ represents the number of samples acquired, this figure also applies to FIG. 26 to 32.

Figure 26:
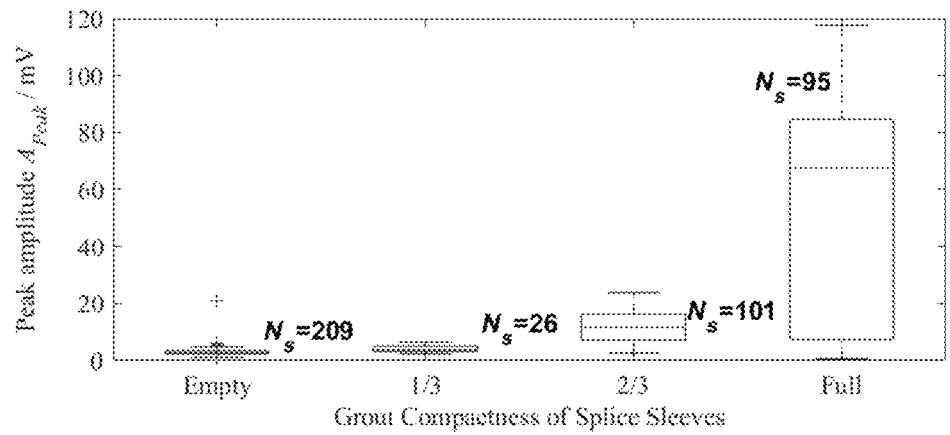

FIG. 26 is the statistical distribution depicting the peak amplitude $A_{Peak}$ in the first half-wave which corresponds to different grout compactness after the grouted bodies were cured for 24 hours.

Figure 27:
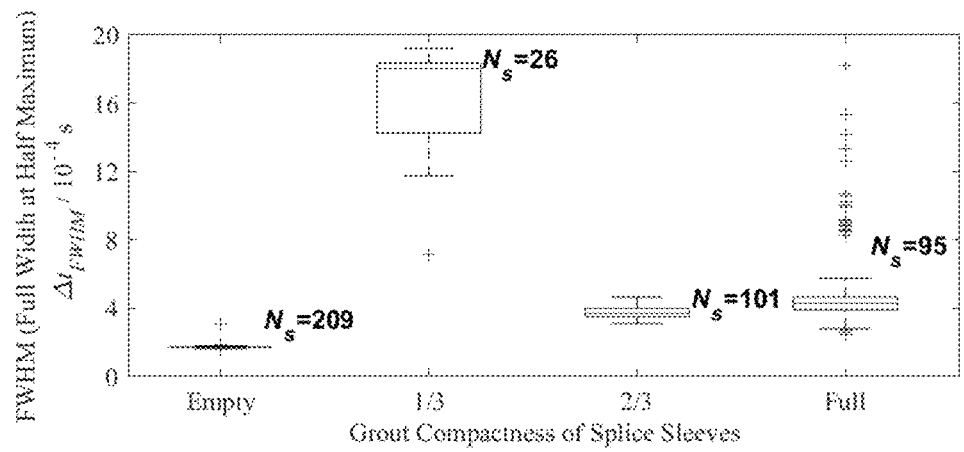

FIG. 27 is the statistical distribution depicting the FWHM (Full Width at Half Maximum) $\Delta t_{FWHM}$ in the first half-wave which corresponds to different grout compactness after the grouted bodies were cured for 24 hours.

Figure 28:
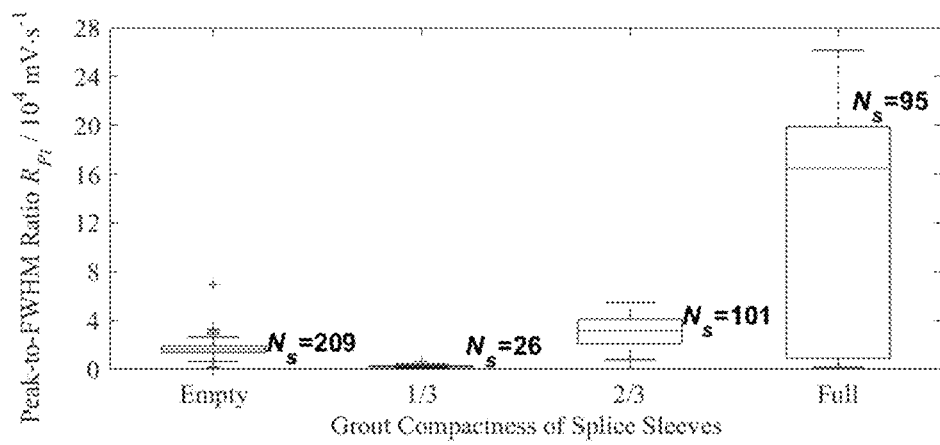

FIG. 28 is the statistical distribution depicting the peak-to-FWHM ratio $R_{Pt}$ in the first half-wave which corresponds to different grout compactness after the grouted bodies were cured for 24 hours.

Figure 29:
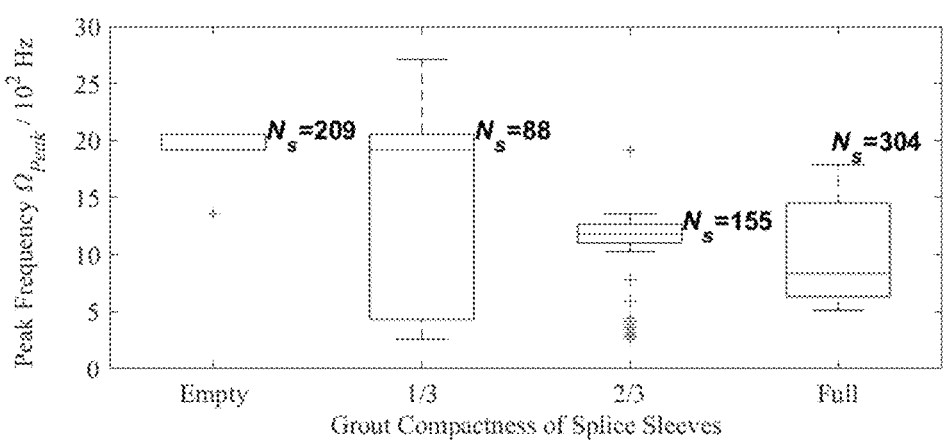

FIG. 29 is the statistical distribution depicting the peak frequency $\Omega_{Peak}$ which corresponds to different grout compactness after the grouted bodies were cured for 48 hours.

Figure 30:
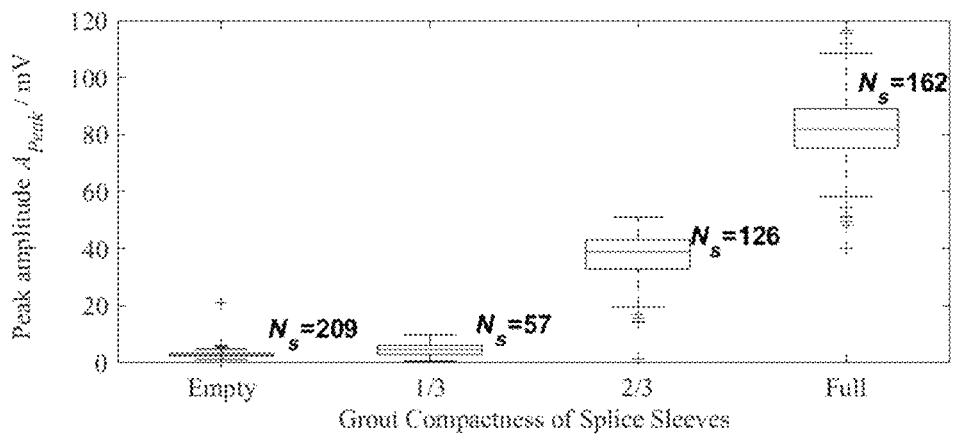

FIG. 30 is the statistical distribution depicting the peak amplitude $A_{peak}$ in the first half-wave which corresponds to different grouted compactness after the grout bodies were cured for 48 hours.

Figure 31:
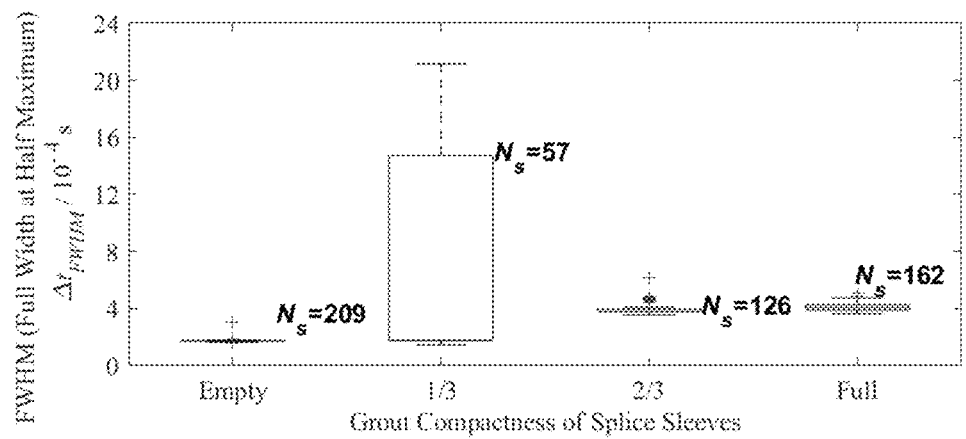

FIG. 31 is the statistical distribution depicting the FWHM (Full Width at Half Maximum) $\Delta t_{FWHM}$ in the first half-wave which corresponds to different grout compactness after the grouted bodies were cured for 48 hours.

Figure 32:
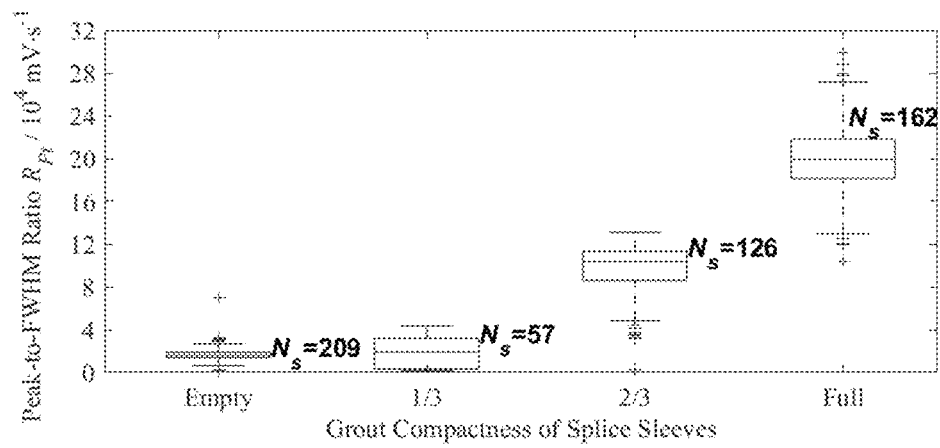

FIG. 32 is the statistical distribution depicting the peak-to-FWHM ratio $R_{Pt}$ in the first half-wave which corresponds to different grout compactness after the grouted bodies were cured for 48 hours.

DETAILED DESCRIPTION

The present invention will be further described and explained below with reference to the drawings and specific embodiments. The technical features of the various embodiments of the present invention can be combined correspondingly without conflicting each other.

The device for detecting grout compactness of splice sleeve proposed by the present invention is aimed at the splice sleeve structure. In a common splice sleeve structure, two rebars are usually connected by a splice sleeve, and the inside of the sleeve is grouted with concrete. After the splice sleeve structure is grouted, the problem of insufficient compactness of this grouting may still exist, which makes the tensile bearing capacity lower than the design value and affects the safety and normal usage of the splice sleeve structure, so it is necessary to provide a detection device which can quantitatively measure the grout compactness of the splice sleeve, to eliminate the potential hazard in construction. The indication of insufficient grout compactness includes: exposure parts of rebar due to insufficient grouting or leakage; or the unfilled cavities causes voids to appear when the grout solidified.

In the present invention, the proposed invention provides a device for detecting grout compactness of the splice sleeve. The basic components of the device include a rigid preloading member, a force transmission rod, a telescopic adjustment member, a vibration sensor, and a data acquisition system.

Among them, the force transmission rod is a rigid rod body, and the force transmission rod is installed on the rigid preloading member through the telescopic adjustment member. The rigid preloading member here is a rigid member used to exert preload to the force transmission rod, and the preloading member is fixed to the wall where the splice sleeve is located by the force transmission rod so that the force transmission rod is inserted through the hole and securely fastened on the surface of the rebar. In this embodiment, in order to ensure the accuracy of vibration transmission, the rigid material parts may be made of steel, and of course, other rigid materials may be used when necessary.

In different buildings, the depth of the sleeves buried in the wall are also different, so the force transmission rod needs to be adjustable to adapt to these different detection scenarios. In the present invention, this is achieved by providing a telescopic adjustment member. The telescopic adjustment member is fixed on the rigid preloading member, which is used to control the movement of the force transmission rod along a direction in perpendicular to the wall, and the end of the force transmission rod can be securely fastened on the surface of the rebar in the sleeve to be tested. The prestress is always maintained between the two throughout the inspection process. The structure of the telescopic adjustment member can adopt various forms, as long as it can adjust the axial displacement of the force transmission rod, and some specific embodiments will be discussed further. In addition, in order to meet the requirement of detection, it is also necessary to fix the vibration sensor on the force transmission rod. Since the force transmission rod and the rebar in the sleeve are securely fastened in the form of prestress, this coupling allows for synchronous vibration. The data sensed by the vibration sensor on the force transmission rod also represents the vibration of the rebar in the sleeve. In addition, in order to obtain the data from the vibration sensor, a data acquisition system needs to be set up. The specific form of the data acquisition system needs to be adjusted according to the type of vibration sensor.

In the present invention, the vibration sensor is either one or more combinations of a strain gauge, a displacement transducer, an accelerometer and a velocity transducer. Among them, the optimal one is the strain gauge, which can be fixed directly to the force transmission rod. The strain gauge is more advantageous due to its sensitivity and simple fixing method, and can serve the detection purpose of the present invention well.

The following provides a preferred embodiment of the device for detecting grouted compactness of the present invention so that those skilled in this technology can better comprehend the present invention.

Embodiment 1

Figure 1:
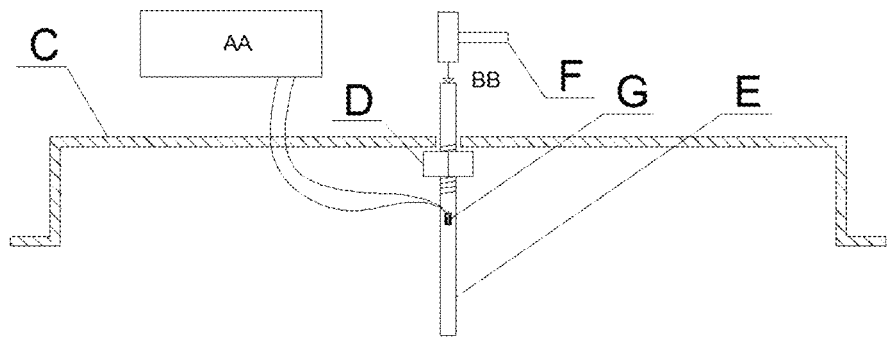
FIG. 1 is a schematic view of a device and structure for detecting grout compactness of splice sleeve.
Figure 2:
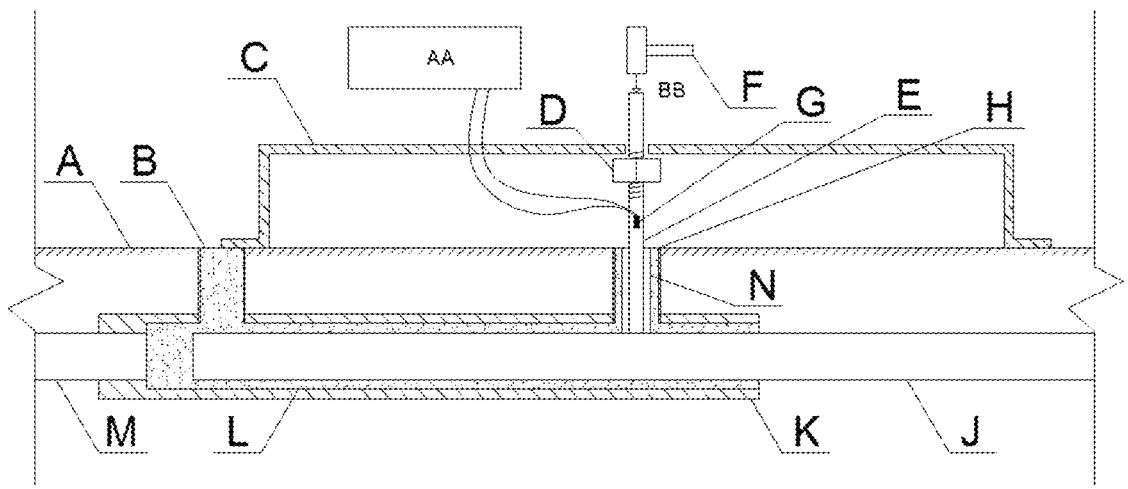
FIG. 2 is a schematic view of a device and installation status for detecting grout compactness of splice sleeve.

FIGS. 1 and 2 show a device and structure for detecting grout compactness of splice sleeve of the present invention. In the splice sleeve structure, the first rebar J and the second rebar M are connected by a sleeve, and the grouted concrete L is injected into the sleeve through the grouting hole H at outer wall K, and any excess will overflow from the grouting extraction hole B.

The grout compactness detection device include a rigid preloading member C made of steel, a nut D, a force transmission rod E, a hammer F, a vibration sensor G. Among them, the preloading member C is a cover-shaped hollow steel structure, which can use steel plate via compression molding method to form a bottomless cylinder or a square cylinder, and the bottom of the cylinder is bent to form an annular flat surface, making preloading member C attachable to the surface of the wall A, and connected and fixed to the wall using adhesives or other fixing parts. A through hole is formed in the cover body of the external rigid preloading member C, and a nut D is fixed on the inner surface of the cover body at the position of the through hole. The force transmission rod E is a rigid rod body, which can be made of steel, and the middle part of the rod body is male threaded. The force transmission rod E passes through the through hole on the cover body and is screwed into the nut D, and the thread on the rod body and the nut D form a screw thread that drives the force transmission rod E to move up and down. In actual use, the end of the force transmission rod E can be adjusted up and down by rotating the force transmission rod E, adapting to different wall surface levels, so that the end of the force transmission rod E is securely fastened on the first rebar J of splice sleeve to be tested. Under different grouting compactness, the vibration signal that can be detected by hammering the BB force to transmission rod E will also be different, and it has a clear correlation with the grout compactness, so the vibration signal can be detected by vibration sensor G, and then this vibration signal is used to estimate the grout compactness of the splice sleeve. Since the force transmission rod E, it will receive the vibration feedback from the internal rebar when it is hammered by the hammer F, so the vibration signal detected by the vibration sensor G is actually the vibration signal of the rebar inside the sleeve. In the present invention, the vibration sensor G is attached to the force transmission rod E, and the end of the force transmission rod E is impacted by the hammer F. In order to ensure accuracy, the force transmission rod E is generally positioned perpendicular to the rebar inside the sleeve, so that the lateral vibration of the rebar will be channeled along the axial direction of the force transmission rod E, and then detected by the vibration sensor G.

Vibration sensor G can be selected according to needs, the signals can reflect the grout compactness of the splice sleeve, and one or more combinations of strain gauge, displacement transducer, accelerometer and velocity transducer are optional. The vibration sensor G also needs to be matched with the data acquisition system AA. In this embodiment, the vibration sensor G uses strain gauges, and the strain gauges need to be connected to a KD5018 integrating charge amplifier and a KD-LP16D data acquisition device, to acquire the time-varying curve of vibration signal data that can reflect the grout compactness.

FIG. 2 shows the installation of the dynamic test device on a splice sleeve. In the splice sleeve to be tested, the grouting extraction hole B and the grouting hole H on the sleeve's outer wall K are both exposed on the surface of the wall A. Therefore, the end of the force transmission rod E can directly pass through the grouting extraction hole B or the grouting hole H and entered the sleeve. The rigid preloading member C is fixed to the surface of the wall A by bolting or pasting, and makes the force transmission rod E securely fastened to the surface of the first rebar J, and then exert a prestress to the force transmission rod E through the nut D, so that the force transmission rod E and the surface of the grouted concrete L will not separate during the test. In this embodiment, in order to ensure detection accuracy, the force transmission rod E is inserted into the sleeve through the grouting hole H.

It should be noted that in the above embodiment, the nut D may be directly welded to the through hole position of the rigid preloading member C, but may also be fixed to the rigid preloading member C in an indirect manner. In addition, the hammer F can be configured as a set, or can be prepared by the user as long as it has rigidity.

Based on the above dynamic test device, a method for hammering preloading test for grouted compactness of splice sleeve structure can also be provided, the steps are as follows:

Step 1: When testing the grout compactness of splice sleeve, the force transmission rod E with the vibration sensor G is extended into the wall body A at the position of the grouting extraction hole B and the grouting hole H on the sleeve's outer wall K, to make the end of the force transmission rod E securely fastened on the grouted body. In this embodiment, when the grouting extraction hole B and the grouting hole H are exposed, the grouted body selects the rebar inside the sleeve. Then, the bottom of the rigid preloading member C is bonded and fixed to the surface of the wall body A by an adhesive. The adhesive can be AB glue. Of course, the rigid preloading member C can also be fixed on the wall body A by expansion screws.

Step 2: Rotate and tighten the force transmission rod E through the nut D which is fixed inside the device, so that the end of the force transmission rod E is securely fastened on the surface rebar of the splice sleeve to be detected, to ensure that the force transmission rod E and rebar will not separate during the test.

Step 3: Exert a force to the end of the force transmission rod E with a hammer F, and acquire the variation curve of the vibration signal over time through the data acquisition system AA connected to the vibration sensor G;

Step 4: Carry out an indoor full-scale model test. The full-scale model is completely consistent with the splice sleeve to be tested. According to the full-scale model, several groups with different grout compactness gradients are set for comparative tests. The gradients of grout compactness can be divided into grouted-free, $\frac{1}{3}$ grouted, $\frac{2}{3}$ grouted, full-grouted, et al . . . . Under the same hammering BB force condition as in Step 3, the same dynamic detection device was used to determine the vibration signal of different grout compactness with variation over time and compare with the variation curve of the vibration signal measured in Step 3, to determine the actual distribution interval of grout compactness, and complete the quantitative judgment of the grout compactness of the splice sleeve. In general, there is a strong correlation between the vibration signal of the strain gauge and the grout compactness, so the measured vibration signal can be compared with the measured data of different grout compactness; and select the interval of the measured data thus determine the actual distribution interval of the grout compactness of the grouted sleeve.

Step 5: After the test is completed, disassemble the device and clean it up for future use.

Embodiment 2

It can be seen from the above embodiment that the device and method for detecting the grout compactness of splice sleeve can determine the actual distribution interval of the grout compactness based on the time-varying curve of the signal under hammering BB. However, in the actual detection process, it is very difficult to visually compare these two changing curves. Therefore, it is necessary to further improve the above detection method to make it easier and feasible to quantitatively determine the grout compactness.

Therefore, based on the aforementioned grout compactness detection method, the present invention provides a further improved device and method for detecting grout compactness of splice sleeve, which mainly improves the extraction of indicators' characteristics from the vibration signal's curve. It is possible to extract the indicators' characteristics representing the compactness of the grouted body in the sleeve from the curve, and judge the compactness of the grouted body by the detected values from the indicators' characteristics. It should be noted that this method does not need to be performed based on the detection device described in the foregoing embodiments. Instead, the following step by step description of the method and devices can be used to know the grouted compactness in the sleeve.

The specific implementation of the improved detection method is described in detail below. In the present invention, the improved method for detecting grouted body compactness of splice sleeve structure is shown in steps S1 to S4:

S1: Securely fastened the rigid force transmission rod to the surface of the rebar in the splice sleeve to be detected, and maintain the prestress between them, so that there will be no separation during the detection process. There are various ways to maintain the prestress between them, without limitation. Similarly, a vibration sensor that vibrates synchronously with the force transmission rod is fixed on it. The vibration sensor can be one or more combinations of a strain gauge, a displacement transducer, an accelerometer and a velocity transducer. In order to ensure accuracy of the detection signal, the force transmission rod is preferably to securely fastened perpendicular to the rebar inside the sleeve, so that the lateral vibration of the rebar will be propagated along the axial direction of the force transmission rod, and then detected by the vibration sensor.

S2: Exert a force along the axial direction of the force transmission rod to the rebar inside the sleeve structure, to make the rebar and the force transmission rod vibrate synchronously; acquire the vibration signal from the force transmission rod under the pulse through the vibration sensor fixed on the force transmission rod. Since the surrounding of the rebar in the sleeve is grouted by concrete, the reinforced concrete is formed when the grouted body is cured, and the rebar will vibrate synchronously with the grouted body. The compactness of grouted body will directly affect the vibration characteristics of the rebar. Therefore, the vibration signal detected by the vibration sensor will actually reflect the compactness of the grouted body. From the vibration signal, the grouted body compactness can be further extracted from the indicators' characteristics values according to the subsequent method. It should be noted that the vibration signal from the force transmission rod under the pulse refers to the time-domain signal detected by the vibration sensor with the vibration caused by the pulse on the rebar transmitted to the vibration sensor as a starting point.

In this step, the specific vibration signal changes as the vibration sensor used changes. If the vibration sensor uses a strain gauge, the vibration signal is the time-domain signal obtained after the electrical signal acquired by the strain gauge are amplified, filtered, and denoised. In addition, if the vibration sensor is an accelerometer, the vibration signal is a velocity signal obtained by integrating the acceleration acquired by the accelerometer. If the vibration sensor is a velocity transducer, the vibration signal is a velocity directly using the velocity signal it acquired. Furthermore, if the vibration sensor is a displacement transducer, the vibration signal is a displacement directly using the displacement signal it acquired.

S3: Since the vibration of the rebar is continuous, the vibration signal acquired by the data acquisition device is actually a waveform composed of a series of discrete points. This signal is a time-domain signal, and the vibration amplitude changes with time. From the waveform of the vibration signal, the parametric values from the indicators' characteristics can be extracted. In the present invention, after research, it has been found that indicators' characteristics that reflect the compactness of the grouted are divided into two types: time-domain indicators and frequency-domain indicator, which are described in detail below.

Figure 3A:
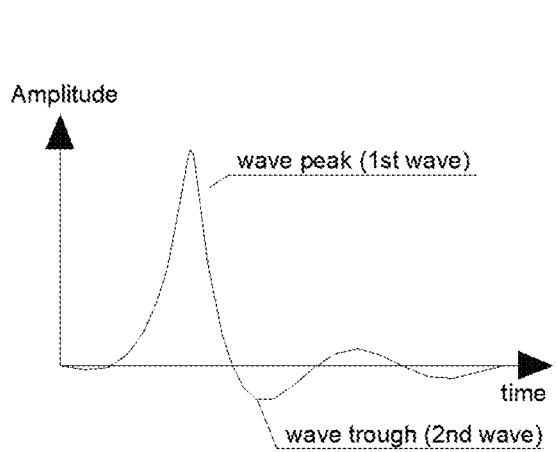
FIG. 3A and FIG. 3B are schematic views of two types of vibration signal curves.
Figure 3B:
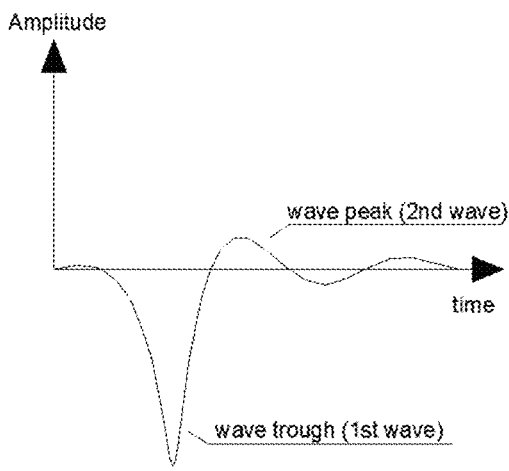

The time-domain indicators mentioned in the present invention include three types, namely, the amplitude of the $N^{th}$ half-wave in the waveform obtained from the time-domain vibration signal, the any width at any of amplitude $\Delta t_{Nwidth}$ and the peak-to-width ratio $R_{Npw}$ at any width at any amplitude $\Delta t_{Nwidth}$, N=1 or 2. Here, the half-wave refers to a wave located on the side of the abscissa axis and having a span of half a period. N=1 or 2, indicating that it can be the first half-wave or the second half-wave in the time-domain signal. It should be noted that due to the different wiring method of the vibration sensor, the $N^{th}$ half-wave detected by it may appear as a wave peak above the abscissa axis or a wave trough below the abscissa axis, both can be regarded as a half-wave. FIG. 3A shows the case where the first half-wave in the waveform curve is a wave peak, and the second half-wave is a wave trough; both of these half-waves can be used to extract the indicators' characteristics. FIG. 3B shows the case where the first half-wave in the waveform is a wave trough, and the second half-wave is a wave peak; both of these half-waves can be used to extract the indicators' characteristics. In the present invention, for ease of description, the any width at any amplitude of the half-wave is also called pulse width $\Delta t_{Nwidth}$, and the ratio of the peak amplitude to the pulse width is also called peak-to-width ratio $R_{Npw}$. In the present invention, the formula for calculating the peak-to-width ratio $R_{Npw}$ of the $N^{th}$ half-wave is as follows:

$$R_{Npw} = \frac{A_{Npeak}}{\Delta t_{Nwidth}}$$

In the formula: $R_{Npw}$ represents the peak-to-width ratio of the $N^{th}$ half-wave; $A_{Npeak}$ represents the peak amplitude of the $N^{th}$ half-wave; $\Delta t_{Nwidth}$ represents the width of the $N^{th}$ half-wave.

For a half-wave, the peak amplitude $A_{Npeak}$ is fixed, but its pulse width $\Delta t_{Nwidth}$ is different at different amplitudes. The above-mentioned pulse width $\Delta t_{Nwidth}$ means the half-wave pulse width at any amplitude. The peak-to-width ratio $R_{Npw}$ refers to the ratio between the amplitude and pulse width $\Delta t_{Nwidth}$ in half-wave, that is, the denominator in the above calculation formula is the half-wave pulse width $\Delta t_{Nwidth}$ at the corresponding amplitude. For example: peak-to-FWHM ratio $R_{pt}=A_{Peak}/\Delta t_{FWHM}$. In the formula: $A_{Peak}$ represents the peak amplitude of half-wave; $\Delta t_{FWHM}$ represents the full width at half maximum (FWHM).

The frequency-domain indicator in the present invention refer to the peak frequency $\Omega_{Peak}$ which is corresponding to the peak amplitude obtained from the frequency-domain vibration signal.

The methods for obtaining the above time-domain indicators are:

After amplifying the electrical signal acquired by the vibration sensor, the filter removes the interference and noise to obtain the time-domain signal; and from this waveform, 3 time-domain indicators can be obtained.

The methods for obtaining the above frequency-domain indicators are:

Perform Fast Fourier Transform (FFT) on the time-domain vibration signal data to obtain the FFT power spectrum, and extract the frequency and amplitude from the power spectrum, and obtain the peak frequency; the frequency corresponding to the maximum vibration amplitude from the frequency-domain is recorded as the peak frequency, which is used as the frequency-domain indicator.

In the present invention, 3 kinds of time-domain indicators and 1 kind of frequency-domain indicator can be used as indicators' characteristics to reflect the grout compactness. In the actual detection process, you can choose one or more combinations.

S4: Since the parametric values from the above indicators' characteristics actually reflect the grout compactness inside the sleeve structure, the parametric values from the indicators' characteristics obtained from the vibration signal in S3, can be used to determine the grout compactness of splice sleeve. For specific determination, it is necessary to recall the distribution interval of the indicators' characteristics parametric values corresponding to the compactness of different grout obtained by the full-scale model in advance.

Rebar, sleeve, and grouted concrete with different model parameters will affect the parametric values reflected by the indicators' characteristics, so the distribution interval of the recalled indicators' characteristics parametric values also needs to be based on the same rebar connection structure as the splice sleeve structure through a full-scale model. The following provides a method for determining the distribution interval of the indicators' characteristics parametric values corresponding to the compactness of different grouted bodies, as follows:

Use the splice sleeve with same model parameters to be tested with different grout compactness, and obtain multiple sets of parametric values from the indicators' characteristics for each grout compactness according to the method described in S1 to S3. In each type of grout compactness, the sample size required for each indicators' characteristics parametric values should meet the statistical requirements, so that it can accurately reflect the distribution interval of the indicators' characteristics parametric values under such grout compactness. After obtaining these parametric values, the data can then be statistically analyzed to obtain the characteristic parametric threshold values at intervals corresponding to the compactness of each grouting. Based on these threshold intervals, the parametric values of the indicators' characteristics obtained from the vibration signal in S3 can be used to determine which threshold interval the parametric value fall in, and then the compactness of the grouted body can be determined.

During prefabrication of the full-scale model, the number of concrete compactness gradients groups can be adjusted, for example, 4 groups of different grout compactness gradients can be set, namely grouted-free, ⅓ grouted, ⅔ grouted, full-grouted. Of course, if higher accuracy of detection is needed, more gradients can be set.

In addition, during the full-scale model test, to determine the threshold value of the indicators' characteristics corresponding to the compactness of different groutings, the prestress exerted on the force transmission rod should be kept as consistent as possible each test. At the same time, during actual detection, the prestress is also consistent with the prestress used in the previous full-scale model test.

In the present invention, there are 4 types of indicators' characteristics, including 3 types of time-domain indicators and 1 type of frequency-domain indicator, all of which can reflect the compactness of the grouted body wrapped on the rebar to a certain extent. If multiple indicators' characteristics are used at the same time, the result of the grouted body compactness of splice sleeve to be tested needs to be determined according to each indicators' characteristics, and synthesized to obtain the final results for the grouted body compactness. In general, the grouted body compactness with the highest number of occurrences, can be selected as the final result. Of course, the weight coefficient of each indicators' characteristics can also be determined at the same time.

From the actual test results, in the present invention, the vibration sensor preferably adopts a strain gauge, and the indicators' characteristics extract preferably adopts the peak-to-FWHM ratio $R_{Pt}$ of the $1^{st}$ half-wave in the waveform curve obtained from the time-domain vibration signal. The peak-to-FWHM ratio $R_{Pt}$ here refers to the half-wave of $\Delta t_{FWHM}$ (Full Width at Half Maximum), which is a straight line at the $\Delta t_{FWHM}$ parallel to the abscissa axis, and it is the distance between the intersection point of the straight line with half-wave. Since the signal's curve actually composed of discrete points, in actual operation, then use the two $\Delta t_{FWHM}$ discrete points that are closest to the half maximum of amplitude.

In the present invention, the original electrical signal acquired by the vibration sensor is relatively weak, so it generally needs to be amplified. Generally, a small-signal/low-noise amplifier (small-signal amplifier or low-noise amplifier, specifically selected according to needs) can be used for amplification. The original signal acquired is an analog signal. After being amplified by a small-signal/low-noise amplifier, it needs to be converted into a digital signal by an analog-to-digital converter and stored in a data acquisition device. The data acquisition device generally adopts a signal detection instrument that matched with the sensor. In addition, there may be more interferences or noises, so it is necessary to remove these interferences and noises through the filter. Filtering and denoising can include one or more combinations of gadgets such as a Wiener filter, a Kalman filter, a band-stop filter, and a low-pass filter. The preferred filtering mode of the present invention, should be composed of a Wiener filter, a Kalman filter, a band-stop filter, and a low-pass filter; the amplified electrical signal is first subjected to Wiener filtering, and then to Kalman filtering to get a smooth signal; next, input the signal into a band-stop filter to suppress the frequency of the powerline interference (in this embodiment, set to 40 Hz~60 Hz), and then filter out the high frequency through a low-pass filter at 3000 Hz. After the filtering using these combined filters, the electrical vibration signal acquired by the strain gauge can be reflected to the greatest extent, which makes it convenient to extract the indicators' characteristics. Of course, if the electrical signal collected by the strain gauge is basically free of noise or interference, then the digital filtering process can be removed. If the original signal value is large enough, the amplification process can also be omitted. Or if the data acquisition device or the slave computer equipped with the strain gauge has in-built amplification or filtering, the output electrical signal output can also be directly used as the vibration signal without additional amplification or filtering.

In addition, the threshold interval of the indicators' characteristics parametric values corresponding to the compactness of different grouted bodies can also be obtained from a threshold lookup table compiled in advance using data derived from a large number of experiments performed earlier. Through the lookup table method, the known parameters such as the sleeve type, the strength of the grout used, the diameter of the rebar and the length of the rebar, the applicable threshold interval can be easily determined.

In addition, an on-site comparison test can be performed to simulate the known grout compactness gradient. Once this is done, and the FEM (Finite Element Method) being used for calculation are in place; the sleeve model, the strength of the grouted body, the rebar length, and diameter can be set under different conditions, and a new set of FEM comparative test data can be obtained; to determine qualitatively and quantitatively the grouted body compactness of the splice sleeve by comparing the results of on-site testing with the FEM comparative test data.

Embodiment 3

The above embodiment 2 shows the present invention improved method for detecting grout compactness of splice sleeve, which can rely upon a variety of detection devices. Although it can also be achieved by the detection device in Embodiment 1, in actual engineering, it is usually necessary to batch-test some amount of the grout compactness of splice sleeves, and since the rigid preloading member of the detection device in Embodiment 1 is directly fixed to the wall, this will cause the force transmission rod with the strain gauges unable to be disassembled quick enough after the test is completed. Therefore, in the present invention, a device for detecting grout compactness of splice sleeve that is more suitable for engineering batch testing is designed. The structure will be described in detail below.

Figure 4A:
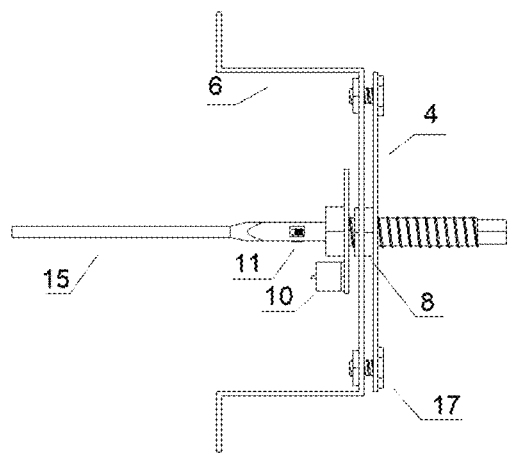
FIG. 4A and FIG. 4B are the 2D and 3D schematic view of an improved device for detecting grout compactness of splice sleeve, respectively.
Figure 4B:
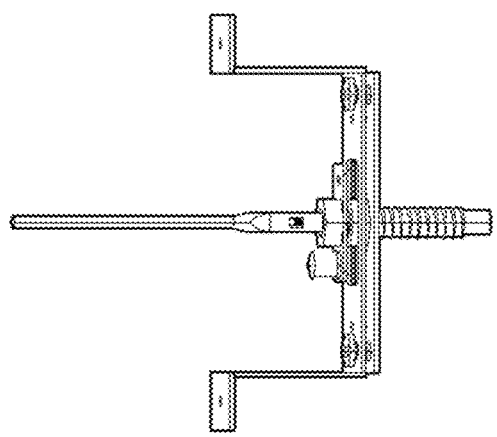

FIG. 4 shows the device for detecting grout body compactness which include a preload applying plate 4, a transducer fixing frame 10, a rigid preloading member 6, a strain gauge 11, a lock 17, and a force transmission rod 16.

Figure 5:
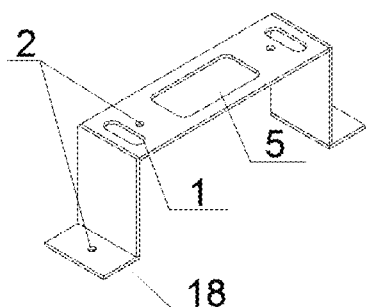
FIG. 5 is a schematic view of a structure for rigid preloading member.

FIG. 5 shows the rigid preloading member 6 is a cover-shaped hollow steel member, which can use the compression molding method to manufacture, and the bottom of preloading member 6 is folded outward at a right angle to form a fixed plane so that it can be installed on the surface of the wall. The rigid preloading member 6 is provided with a slot 1, a small hole 2, a central hole 5, and a wing foot 18; the slot 1 is opened one at each end; the small hole 2 is opened two at each end; FTR (Force Transmission Rod) through-hole 3 is used for the force transmission rod 16 to pass through. The rigid preloading member 6 is connected and fixed to the wall body by using adhesives or expansion screws. The central hole 5 on the top of rigid preloading member 6 is for passing the transducer fixing frame 10 fixed on the force transmission rod 16. Slot 1 on the top of rigid preloading member 6 is to enable lock 17 to pass through slot 1 on the preload applying plate 4 to achieve the effect of exerting prestress to the force transmission rod 16. The small hole 2 on the top of rigid preloading member 6 is used for positioning or passing through the transducer cable. The rigid preloading member 6 can be fixed to the wall by using nails or screws through the small holes 2 in the wing foot 18 or fixed to the surface to be measured using glue, or both.

Figure 8:
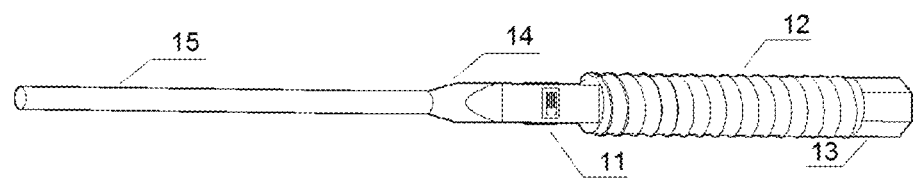
FIG. 8 is a schematic view of a structure for force transmission rod.

FIG. 8 shows the force transmission rod 16 which has a multi-stage structure, sequentially divided into a male thread with a section 12, a hexagonal section 13, a transition section 14, and a round section 15; the entire force transmission rod 16 is integrally made of steel. The diameter of the round section 15 should be smaller than the grouting extraction hole of the sleeve to facilitate insertion into the sleeve. The transition section 14 has a flat surface where the strain gauge 11 is attached. The male thread at section 12 is used to install and cooperate with the rigid preloading member 6, and is also used to assemble the transducer fixing frame 10, and the hexagonal section 13 can use the wrench to screw to the force transmission rod 16.

Figure 6:
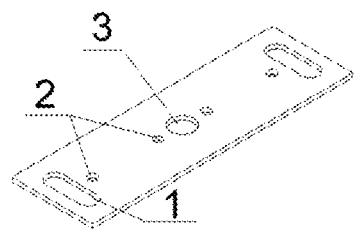
FIG. 6 is a schematic view of a structure for preload applying plate.

FIG. 6 shows the preload applying plate 4 which is a rigid plate made of steel. A slot 1, a small hole 2 and an FTR through-hole 3 are opened on the preload applying plate 4 which is corresponding to the rigid preloading member 6. The FTR through-hole 3 is for passing the force transmission rod 16. In the present invention, a locknut is coaxially welded on the FTR through-hole 3, and the male thread section 12 of the force transmission rod 16 matches with the locknut; rotate hexagonal section 13 adjust the displacement of force transmission rod 16 along its own axis. Slot 1 on the preload applying plate 4 corresponding to slot 1 on the rigid preloading member 6 for mounting the lock 17. Small holes 2 on the preload applying plate 4 correspond to small holes 2 on the rigid preloading member 6, which can be passing through the transducer cable or positioning function.

Figure 7:
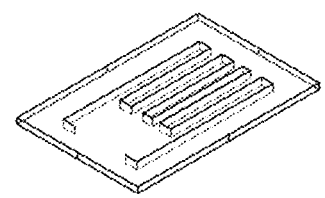
FIG. 7 is a schematic view of a structure for strain gauge.

FIG. 7 shows the strain gauge 11 which is planar, and can be directly attached to the flat surface of the transition section 14.

Figure 9:
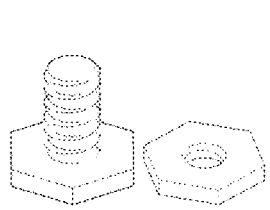
FIG. 9 is a schematic view of a structure for lock.

FIG. 9 shows the lock 17 which is composed of a bolt and a nut. The bolt can be fit into the corresponding slot 1 on the preload applying plate 4 and the rigid preloading member 6; the size of the bolts is fit to slot 1, and the nut can screw to the bolt. Thus, the bolts can be used to lock-in the preload applying plate 4 and the rigid preloading member 6 while ensuring that the relative spacing can be adjusted, and the spacing adjustment direction is consistent with the axial direction of the force transmission rod 16.

Figure 10:
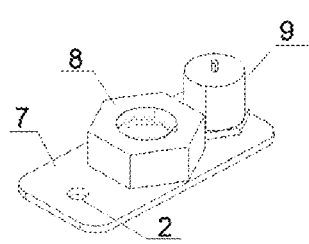
FIG. 10 is a schematic view of a structure for transducer fixing frame.

FIG. 10 shows the transducer fixing frame 10 which is a rigid object composed of a transducer tray 7, a nut 8, and small holes 2. The transducer fixing frame 10 is installed on the male thread 12 of the force transmission rod 16 through nut 8. Through the small holes 2 on the left and right of the transducer tray 7, the accelerometer 9, velocity transducer, or displacement transducer can be installed on the transducer fixing frame 10, the transducer fixing frame 10 can install or remove the attached transducer, and either single or two or more transducers can be installed. The strain gauge 11, accelerometer 9, velocity transducer, or displacement transducer output electrical signals, and the transducer needs to be calibrated before use to obtain the required physical quantity.

Figure 11:
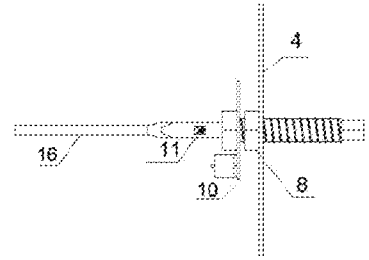
FIG. 11 is a schematic view of the assembly for detachable part.
Figure 12:
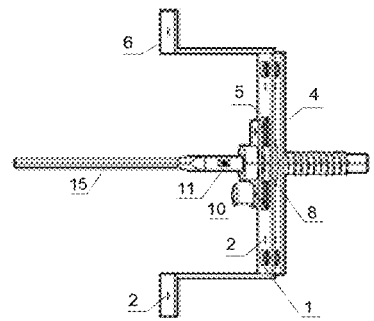
FIG. 12 is a schematic view of the structure after the detachable part is assembled into the rigid preloading member.
Figure 13:
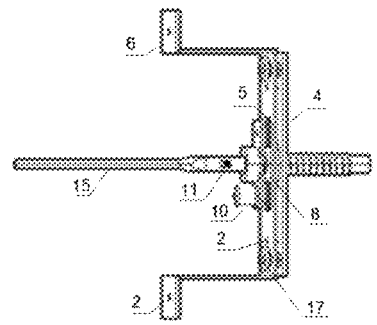
FIG. 13 is a schematic view of the structure after the detachable part and the rigid preloading member are securely fastened by the lock.
Figure 14:
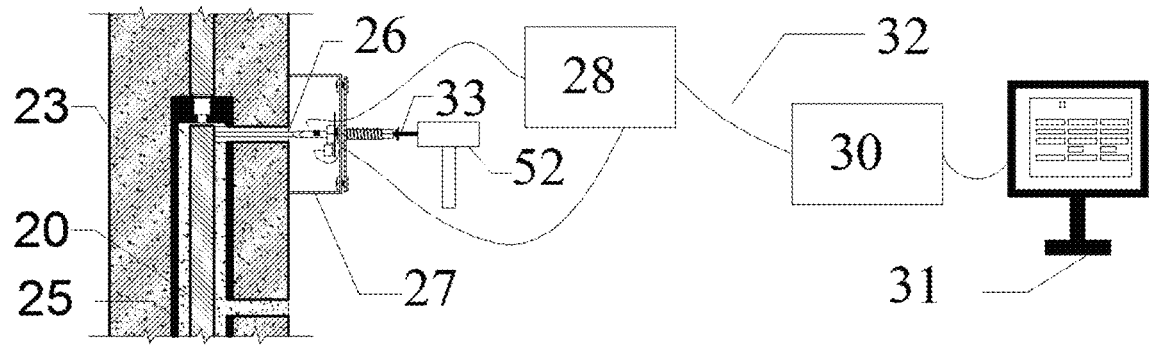
FIG. 14 is a schematic view of detection status from an improved device for detecting grout compactness of splice sleeve.

The preload applying plate 4, the transducer fixing frame 10, the strain gauge 11, and the force transmission rod 16 are combined to form the detachable part as shown in FIG. 11, and the rigid preloading member 6 and the lock 17 have not been installed at this time. Subsequently, the detachable part can be installed on the rigid preloading member 6 as shown in FIG. 12, the slot 1 at both ends is fixed by lock 17 as shown in FIG. 13. FIG. 14 shows an example of install the accelerometer 9 on the transducer fixing frame 10, the corresponding transducer cable 32 is used to connect the small-signal/low-noise amplifier 28 to the strain gauge 11 and accelerometer 9 on the force transmission rod 16; and connect the small-signal/low-noise amplifier 28 to the data acquisition device 30 then to master computer 31 to form a circuit route. The data acquisition device 30 of the vibration sensor is connected to the master computer 31 through wired or wireless communication, and the vibration signal data is stored in master computer 31. The master computer 31 generally uses computer. On the wall surface where the splice sleeve to be tested is located, the wing foot 18 on the rigid preloading member 6 are firmly fixed on the wall surface using AB glue or expansion screws. Then, the detachable part shown in FIG. 11 is passed through the central hole 5 of the rigid preloading member 6 and then locked by lock 17 to form a complete detection device 27. In actual use, the end of the force transmission rod 16 can be adjusted up and down by rotating the force transmission rod 16, or at the same time, it also can cooperate with lock 17 to adapting to different wall surface level, so that the end of the force transmission rod 16 is securely fastened on the rebar surface to be tested of splice sleeve structure.

It should be noted that, in this embodiment, the splice sleeve applicable to the detection device are varies. As shown in FIG. 15 are three types of splice sleeve, FIG. 15A is a half-grout sleeve, including threaded hole 19, rebars 20, grouting extraction joint 21, and grouting joint 22; FIG. 15B is the rebar anchoring grouting structure, including rebars 20 including grouting extraction joint 21, grouting joint 22, concrete 23; FIG. 15C is a full-grout sleeve, including rebars 20, grouting extraction joint 21, and grouting joint 22, cover 24. Here, the grouting extraction joint 21 and the grouting joint 22 are also referred to as the grouting extraction hole and the grouting hole in Example 1, and have the same meaning. If the grouting extraction joint 21 is not exposed on the wall surface, a borehole 26 is drilled from the wall surface towards the sleeve. The borehole 26 penetrates grouting extraction joint 21, and the end of the force transmission rod 16 can pass through borehole 26 and securely fastened to the rebar 20 inside the sleeve.

In the above detection device 27, the rigid preloading member 6 can be fixed in batches on the wall to test the splice sleeves. After the detection of a sleeve is completed, the detachable part can be released by lock 17, and the detachable part is drawn away from the rigid preloading member 6. The detachable will do a next test point to improve the detection efficiency.

After the installation of the detection device 27 is completed, a force 33 can be applied to the hexagonal section 13 of the force transmission rod 16 to obtain a vibration signal. Here, a hammer 52 may be used to apply a force 33 to the device 27. However, as a preference, in another preferred embodiment, a manual impact hammer 49 or an auto impact hammer 49 is used to apply the force 33 so that the force 33 can be applied multiple times and the signals will be acquired simultaneously.

FIG. 16 shows the manual impact hammer 49 which is a hammering device installed on the force transmission rod 16. The components of the hammering device include a connecting-rod 41, a spring 43, a mass 44, and a fixing frame 45. The fixing frame 45 is a cylindrical steel block with a bottom-opening assembly hole, and inside of the assembly hole is the female thread. The male thread section 12 and the hexagonal section 13 on the top of the force transmission rod 16 extend into the assembly hole of fixing frame 45. The male thread section 12 and the assembly hole of the fixing frame 45 form a threaded fit. Spring 43 and mass 44 are installed in the assembly hole. The top of the fixing frame 45 has a hole with an aperture larger than that of the connecting-rod 41. The connecting-rod 41 extends from the hole of the top of the fixing frame 45 into the assembly hole and is connected to the mass 44 through a hinge 46 for fixing. Spring 43 is located between mass 44 and the inner top of the assembly hole. The connecting-rod 41 can pull the mass 44, and the mass 44 compresses the spring 43 during the process of being pulled by the connecting-rod 41 toward the top of the fixing frame 45. While the connecting-rod 41 is not constrained by an external force, the compression elastic force of spring 43 will be used to push the mass 44 to exert a force 33 on the hexagonal section 13 of the force transmission rod 16 along the axial direction.

In order to ensure that the force 33 can be propagated along the axial direction of the force transmission rod 16, a piston ring 34 may be further installed on the side of the mass 44, and the mass 44 form a piston structure with the assembly hole of the fixing frame 45 through the spring 43 that can restrict the moving direction of the mass 44 to only along the axial direction of the assembly hole.

The force 33 generated by the spring 43 through the mass 44 can be converted to F=k x, that is, F is the force, k is the stiffness, and x is the compression distance. According to the different requirements of the test for the force 33, the springs 43 with different stiffness k are changed; by changing the extension or compression distance x of the spring 43, the springs 43 with different displacements are adjusted so that different force 33 are applied to the mass 44.

The connecting-rod 41 in the above-mentioned manual impact hammer 49 needs to be manually pulled by an operator, and its pulling distance will determine the magnitude of the force 33. Furthermore, in order to facilitate control, an automatic applying force device is further provided on the basis of the manual impact hammer 49, thereby forming an auto impact hammer 49. The automatic applying force device has a displacement output end, which is used to push the connecting-rod 41 and release the connecting-rod 41 after compressing the spring 43 quantitatively. In a preferred embodiment of the present invention, as shown in FIGS. 17 and 18, the automatic applying force device include a motor 39, a cam 40 and a cushion block 42, the cushion block 42 is placed on the fixing frame 45 and the cushion block 42 can be mounted with a motor 39. The cam 40 is mounted on the output shaft of the motor 39. The top of the connecting-rod 41 has a bent portion, and the rotation path of the cam 40 passes through the bent portion. Therefore, when the cam 40 rotates, the connecting-rod 41 is pushed upward, and the spring 43 compresses and stores energy. When rotating to a certain angle, the cam 40 is disengaged from the bending portion of the connecting-rod 41, the connecting-rod 41 is not subjected to external force, and then the compression energy of the spring 43 is used to push the mass 44 to exert a force 33 on the hexagonal section 13 of the force transmission rod 16 along the axial direction. When the cam 40 continues to rotate under the action of the motor 39, the process will be repeated, so that the same magnitude of force 33 can be continuously applied.

The magnitude of the force 33 exerted by the auto impact hammer 49 can be changed by changing the stiffness k of the spring 43, the compression distance x of the spring 43, the weight of the mass 44, or the greatest radial of the cam 40. The frequency of the force 33 exerted by the auto impact hammer 49 can be realized by changing the rotation speed of the motor 39.

Based on the detection device in this embodiment, the present invention can provide a preferred method for detecting the grouted compactness of splice sleeve structure, the steps are as follows:

Step 1: The corresponding transducer cable 32 is used to connect the small-signal/low-noise amplifier 28 to the strain gauge 11 and accelerometer 9 (if any) on the force transmission rod 16; connect the small-signal/low-noise amplifier 28 to the data acquisition device 30 and then to master computer 31 to form a circuit route, and then the small-signal/low noise amplifier 28 and the data acquisition device 30 are turned on.

Step 2: Assemble the force transmission rod 16 already provided with the strain gauge 11, the preload applying plate 4 and et al. into the form shown in FIG. 11.

Step 3: Locate the wall of the splice sleeve to be tested to match the two small holes 2 on the wing foot 18, and then use an impact driver drilling at the marked marks on the concrete 23. A borehole 26 is drilled from the surface of the wall toward the sleeve, and the borehole 26 penetrates the grouting extraction joint 21 to check and confirm that the surface of the rebar in the sleeve has been exposed. Next, apply glue through the wing foot 18 on the rigid preloading member 6, and then fix the expansion screws into the wall through the small holes 2 on the wing foot 18, so that the rigid preloading member 6 can be firmly fixed to the wall that the splice sleeve to be tested.

Step 4: Install the detachable part to the rigid preloading member 6 which has been fixed on the wall, and form the detection device 27 through fixed the lock 17; through the clockwise or counterclockwise rotation of the lock 17 or force transmission rod 16 itself, the end of the force transmission rod 16 is securely fastened on the rebar surface, and the prestress can be controlled by adjusting the lock 17 or force transmission rod 16.

Step 5: As shown in FIG. 14, the installed detection device 27 exerts a force 33 to the hexagonal section 13 on the force transmission rod 16. The strain gauge 11 and accelerometer 9 on the force transmission rod 16 sense the electrical vibration signal reflected by the pulse from the rebar inside the splice sleeve, and the small-signal/low-noise amplifier 28 amplifies the originally weak instantaneous electrical signal and acquired the electrical vibration signal by the data acquisition device 30, and then stored in the master computer 31.

Step 6: Repeat Step 5 for a few times, and the vibration signal of multiple sets of strain gauge 11 and accelerometer 9 are acquired and stored in the master computer 31. Then, the data in the master computer 31 is programmed with MATLAB as the platform, and the acceleration signal output by the accelerometer 9 is first integrated into a velocity signal, and then velocity signal acquired from the strain gauge 11 and the accelerometer 9, both of them are time-domain signals with interference, are subjected to Wiener filtering, Kalman filtering, band-stop filtering, and low-pass filtering to extract effective signal information as much as possible.

In this embodiment, the Wiener filter may use a Wiener speech enhancement method to suppress noise and enhance the target frequency.

The electrical vibration signal after Wiener filtering is inputted into the Kalman filter. The Kalman filter uses an improved Kalman filter. Knowing the acquired electrical vibration signal, a vector is formed through the discrete-time windows, and then Amp is the amplitude of output electrical signal, and $\hat{Amp}^-$ is the predicted state estimate of electrical signal value, the algorithm steps are as S41-S46, where:

S41: For the $i^{th}$ sampling point of $x_i$ in the amplified electrical signal value, a filter window of size $N_{fw}$ is set with the $i^{th}$ sampling point as the center, and a vector $Data_i$ composed of all sampling points in the filter window is obtained; the predicted state estimate of electrical signal value are $$\hat{Amp}^- = \text{Däta} = \frac{1}{N}\sum_{j=1}^{N_{fw}} \text{Data}_i^j;$$

among them, Däta is the average of all sampling points in the current filter window, $\text{Data}_i^j$ represents the signal value of the $j^{th}$ sampling point in the vector $Data_i$, $j \in [1, N_{fw}]$.

S42: Covariance matrix of the observation noise $$R = \frac{1}{N-1}\sum_{j=1}^{N_{fw}} |\text{Data}_i^j - \text{Däta}|^2;$$

S43: Calculate optimal Kalman gain $$K = \frac{|\hat{Amp}^-| \cdot H^T}{H \cdot |\hat{Amp}^-| \cdot H^T + R};$$

among them, H is the observation matrix, T means transpose.

S44: Calculate the amplitude of the output electrical signal after filtering at the $i^{th}$ sampling point:

$$\hat{Amp} = \begin{cases} -\{|\hat{Amp}^-| + K \cdot (|\text{Data}_{x_i}| - H \cdot |\hat{Amp}^-|)\}, & \hat{Amp}^- < 0 \text{ and } \text{Data}_{x_i} < 0 \\ |\hat{Amp}^-| + K \cdot (\text{Data}_{x_i} - H \cdot \hat{Amp}^-), & \text{others} \end{cases}$$

In the formula: $\text{Data}_{x_i}$ represents the sampling value of the $i^{th}$ sampling point $x_i$;

S45: Before filtering the next sampling point, update the predicted state estimate of electrical signal value $\hat{Amp}^- = (1-K \cdot H) \cdot \text{Däta} + Q$, where Q is the state transition covariance matrix; meanwhile, i=i+1.

S46: Repeat steps S42 to S45 for the remaining sampling points in the amplified electrical signal in sequence to complete Kalman filtering;

Input the electrical vibration signal data after Kalman filtering into the band-stop filter to suppress the powerline interference frequency in the band of 40 Hz to 60 Hz.

Finally, the band-stop filtered signal passes through a low-pass filter at 3000 Hz to filter out high-frequency signals with no valid information to obtain time-domain data.

Step 7: The amplitude of the $N^{th}$ half-wave in the waveform curve obtained from the time-domain vibration signal; the any width at any of amplitude $\Delta t_{Nwidth}$, and the peak-to-width ratio $R_{NpW}$ at any width at any amplitude $\Delta t_{Nwidth}$; where N=1 or 2.

Step 8: Perform FFT on the new time-domain data to obtain the FFT power spectrum, and extract the frequency and amplitude in the power spectrum, and obtain the peak frequency; the peak frequency is a frequency corresponding to the maximum power amplitude in the frequency-domain.

Step 9: Taking any one or more of the peak amplitude $A_{Npeak}$, the pulse width $\Delta t_{Nwidth}$, the peak-to-width ratio $R_{NpW}$ and the peak frequency as the indicators' characteristics. According to the parametric values obtained from Step 7 to Step 8, based on the distribution interval of the indicators' characteristics parametric values corresponding to the compactness of different grouted body, determine the compactness of the grouted body in the splice sleeve to be tested.

In this embodiment, N is preferably taken as 1, and the indicators' characteristics are preferably the peak-to-FWHM ratio $R_{Pt}$ of the $1^{st}$ half-wave on the waveform.

In order to prove the effectiveness of the above-mentioned detection method in this embodiment, a full-scale model test was conducted with a single strain gauge as a vibration sensor. In full-scale model testing, several grout bodies with different compactness are injected into the several splice sleeve to be tested with the same model parameters. In this embodiment, 4 groups of gradients grouted with different compactness are set, which is expressed in the grouted body 25 with different inside sleeve's height, which is grout-free, ⅓ grouted, ⅔ grouted, and fully-grouted, which means that the grouted height of the inner cavity of the sleeve is 0, ⅓, ⅔ and full, respectively, are shown as A to D in FIG. 19. The grouting method in the splice sleeve structure is as follows:

(1) The sleeve uses Beijing Sida Jianmao J M rebar half-grout sleeve, the type of sleeve is GT14, the connecting rebar uses HRB400 [hot-rolled ribbed bar with 400 MPa (58 ksi) yield strength], and the nominal size 14 mm rebar is used for configuration.

(2) The grout of the splice sleeve is using the non-shrink high-early strength cement to make the grouted body 25. The production process is as follows:

a) Calculate the volume of the grouted body 25 needed, weigh the corresponding amount of water and cement, and put all the water into the container first.

b) After putting all the water into the container, first mix 70% cement and stir for about 2 minutes.

c) After stirring, the remaining 30% of the cement is mixed in. After stirring evenly, until no aggregated particles are observed, then take about 5 minutes of rest to exhaust the bubbles.

d) Put the agitated grout 25 into a conical mold (with dimensions of 100 mm base diameter, 70 mm top diameter, and 60 mm height) and place it on a tempered glass table, and then the flow table test to meet the 300 mm slump.

e) A set of three gang prism mold can produce three 40×40×160 mm rectangular test blocks, apply silicone oil to the prism mold and use 8 sets of prism mold to make 24 test blocks (8 groups). The compressive and flexural strength of each group is based on the average of 3 rectangular test blocks.

f) In order to ensure the fluidity of the grout 25, starting from the time when the cement and water are mixed, all operations need to be completed within 30 minutes, otherwise the grout 25 must be re-made.

(3) Use a manual grouting pump and use the prepared grout 25 to start grouting from the grouting joint 22 to prepare splice sleeve structure with a free-grouted body, ⅓ grouted body, ⅔ grouted body, and full-grouted body. For a sleeve filled with full-grout, wait until the grouting material emerges from the grouting extraction joint 21, then stop the grouting operation, and use a rubber cork to block the grouting joint 22 and the grouting extraction joint 21; other sleeve models are filled with the grouting material to a predetermined height, then grouting is stopped, and rubber cork is used to block the grouting joint 22 and the grouting extraction joint 21.

For the production of 8 groups of test blocks, at 24 h, 32 h, 48 h, 72 h, 8 d, 14 d, and 28 d after grouting, use a concrete flexural test machine to conduct a destructive test on the test blocks to obtain the corresponding compressive strength $\sigma_c$ as shown in FIG. 20. This shows that the grouted body 25 has reached nearly 50% strength after being filled into the sleeve for 24 hours, and basically reached nearly 80% strength after 48 hours, the strength development rate then start decreasing. Therefore, considering the balance of efficiency and accuracy, in the detection methods of the embodiments of the present invention, the detection time needs to be set after the grouted body 25 in the sleeve is cured, and the curing time is preferably 24 h to 48h or more; the experiment in this embodiment, two groups with 24h and 48 h curing were set up.

An iron hammer 52 are given the force 33 to different compactness gradients grouted of rebar inside the sleeve, and then the electrical vibration signals results obtained by the strain gauge 11 on the force transmission rod 16 is subjected to the aforementioned Wiener filtering, improved Kalman filtering, band-stop filtering and low-pass filtering, a new time-domain signal is obtained. After that, the short-time Fourier transform the time-domain signal and produced the Wavelet power spectrum, and then the frequency-domain graph with frequency (unit: kHz) and amplitude (unit: mV) can be extracted. The results of the models with free-grouted, ⅓ grouted, ⅔ grouted, and full-grouted are shown in FIG. 21 to 24, respectively. FIG. 21 to 24 of A, B, C corresponding to the vibration time-domain graph (abscissa axis start point has been shifted), Wavelet power spectrum, and frequency-domain graph.

Therefore, according to the above detection method, multiple sets of parametric values of the indicators' characteristics can be obtained for each type of grouted body compactness. In each type of grouted body compactness, the sample size required for each indicators' characteristics parametric values should meet the statistical requirements, so that it can accurately reflect the distribution interval of the indicators' characteristics parametric values under such grouted body compactness. After obtaining these parametric values, the indicators' characteristics parametric values can be statistically analyzed to obtain the characteristic parameter threshold value interval corresponding to the compactness of each grouted.

After the grouted body 25 was cured for 24 hours, a total of 431 tests were carried out on the sleeve models corresponding to the grouted body 25 with different grouted compactness, and statistical analysis was carried out to obtain the statistical distribution diagram of the parametric values of the indicators' characteristics. There are 4 indicators' characteristics, including 3 time-domain indicators and 1 frequency-domain indicator. FIG. 25 shows the frequency-domain indicator with the peak frequency $\Omega_{Peak}$ obtained from the frequency-domain waveform; the 3 time-domain indicators are the peak amplitude $A_{peak}$, FWHM $\Delta t_{FWHM}$, and the peak-to-FWHM ratio $R_{Pt}$ of the $1^{st}$ half-wave in the waveform and the results are shown in FIG. 26 to 28 respectively.

After the grouted body 25 was cured for 48 hours, a total of 554 tests were carried out on the sleeve models corresponding to the grouted body 25 with different grouted compactness, and statistical analysis was carried out to obtain the statistical distribution of the parametric values of the indicators' characteristics. There are 4 indicators' characteristics, including 3 time-domain indicators and 1 frequency-domain indicator. FIG. 29 shows the frequency-domain indicator with the peak frequency $\Omega_{Peak}$ obtained from the frequency-domain waveform; the 3 time-domain indicators are the peak amplitude $A_{Peak}$, FWHM $\Delta t_{FWHM}$, and the peak-to-FWHM ratio $R_{Pt}$ of the $1^{st}$ half-wave in the waveform and the results are shown in FIG. 30 to 32 respectively.

Based on these threshold intervals, the parametric values of the indicators' characteristics obtained from the vibration signal during the actual detection process where the threshold interval's parametric values falls in, and then the compactness of the grouted body corresponding to the threshold interval is used as the splice sleeve structure to be detected and get results, thus realizing the quantitative detection of the grouted body compactness.

However, it can be found from the above results that the peak-to-FWHM ratio $R_{Pt}$ is more advantageous than the other three indicators' characteristics, and its parametric values distribution interval under different grouted compactness has more significant differences, so it can respond more accurately to the compactness of grouted inside the sleeve. Therefore, the indicators' characteristics in the present invention primarily prefer the peak-to-FWHM ratio $R_{Pt}$ of the $1^{st}$ half-wave on the waveform. Of course, for accurate analysis judgment, more feature indicators can be combined, and weight coefficients can be appropriately assigned to the respective results, so as to obtain a more accurate result of grouted compactness.

It should also be noted that, according to the foregoing, although strain gauges are used as vibration sensors for description here, in fact, accelerometer, velocity transducer, and displacement transducer can all be used to achieve the same function and can be combined as needed.

The above-mentioned embodiments are only a preferred solution of the present invention, but they are not intended to limit the present invention. Those skilled laborers in the technical field can make various changes and modifications without departing from the spirit and scope of the present invention. Therefore, any technical solution obtained by adopting the method of equivalent replacement or equivalent transformation falls within the protection scope of the present invention.

What is claimed is:

1. A device for detecting grout compactness of splice sleeve, wherein the device comprises a rigid preloading member, a force transmission rod, a telescopic adjustment member, a vibration sensor, and a data acquisition system;
    the force transmission rod is a rigid rod body, which is installed on a rigid preloading member by means of the telescopic adjustment member; the rigid preloading member is used to fix the force transmission rod to the wall where the connecting structure of the splice sleeve is located, and the telescopic adjustment member is fixed to the rigid preloading member and used to control the movement of the force transmission rod along a direction in perpendicular to the wall, so that the end of the force transmission rod is securely fastened to a rebar surface in a splice sleeve to be detected; the vibration sensor is fixed to the force transmission rod, and the data acquisition system is used to acquire vibration signals from the vibration sensor.

2. The device for detecting grout compactness of splice sleeve according to claim 1, wherein the rigid preloading member is a cover-shaped hollow steel member, and the bottom is fixed on the wall surface where the splice sleeve structure to be tested is located.

3. The device for detecting grouted compactness of splice sleeve according to claim 2, wherein a through hole is formed in the cover of the rigid preloading member; the telescopic adjustment member is a nut, which is fixed at the through hole position of the cover body; the middle part of the force transmission rod are male threaded, passes through the through hole on the cover body and is screwed into the nut; the thread on the rod body and the nut form a threaded fit for driving the force transmission rod to move axially.

4. The device for detecting grout compactness of splice sleeve according to claim 1 or 3, wherein the detection device comprising a hammer for exerting an impact to the end of the force transmission rod.

5. The device for detecting grout compactness of splice sleeve according to claim 1, wherein splice sleeve structure, the grouting extraction hole and the grouting hole on the outer wall of the sleeve are both exposed at the wall surface; the end of the force transmission rod passes through the grouting extraction hole and enters the inside of the sleeve, and supported on the surface of the rebar.

6. The device for detecting grout compactness of splice sleeve according to claim 1, wherein the vibration sensor is one or more combinations of a strain gauge, a displacement transducer, an accelerometer and a velocity transducer.

7. The device for detecting grout compactness of splice sleeve according to claim 1, wherein the vibration sensor is a strain gauge; the strain gauge attached and fixed on the force transmission rod.

8. The device for detecting grout compactness of splice sleeve according to claim 1, wherein the telescopic adjustment member comprising a preload applying plate and a lock member; the force transmission rod and the preload applying plate is rigid connection and fixed, and the preload applying plate and the rigid preloading member form a lock with an adjustable relative spacing through at least one lock member; the spacing adjustment direction is axially consistent with the force transmission rod.

9. The device for detecting grout compactness of splice sleeve according to claim 8, wherein the preload applying plate is provided with a through hole, and a locknut is fixed at the position of the through hole; the force transmission rod at the middle of the rod body are male threaded, passes through the through hole on the preload applying plate and is screwed into the locknut; the thread on the rod body and the locknut form a threaded fit for driving the force transmission rod to move axially.

10. The fixing frame with a bottom-opening assembly hole according to claim 8, wherein the thread on the force transmission rod and the assembly hole of fixing frame form a threaded fit; a spring and a mass are placed in the assembly hole, and the connecting-rod extends from the hole of the top of the fixing frame into the assembly hole and is connected to the mass; the mass compresses the spring when the connecting-rod is pulled toward the top of the fixing frame; while the connecting-rod is not constrained by an external force, the compression elastic force of spring be used to push the mass to exert a force on the top of the force transmission rod along the axial direction.

11. The device for detecting grout compactness of splice sleeve according to claim 10, wherein the hammering device comprises of an automatic applying force device; the automatic applying force device has a displacement output end, which is used to push the connecting-rod and release the connecting-rod after compressing the spring quantitatively.

12. The device for detecting grout compactness of splice sleeve according to claim 1, wherein the data acquisition system comprises of a small-signal/low-noise amplifier and a master computer; the vibration sensor is connected to a small-signal/low-noise amplifier, a data acquisition device, and connected to the master computer.

13. A method for detecting grout compactness of splice sleeve, wherein the device used in the method comprises a preloading member, a nut, a force transmission rod, a hammer and a vibration sensor; the preloading member is a cover-shaped hollow rigid member, and its bottom is fixed around the wall where the splice sleeve to be tested is located; the preloading member is provided with a through hole, and a nut is fixed at the position of the through hole; the force transmission rod is a rigid rod body, and the middle part of the rod body is male threaded, the force transmission rod passes through the through hole on the preloading member body and is screwed into the nut; the thread on the rod body and the nut that can drives the force transmission rod to move up and down; the end of the force transmission rod is tightly supported on the grouted body of splice sleeve to be detected; the vibration sensor is fixed to the force transmission rod; the hammer is used to exert an impact to the end of the force transmission rod;

the step by step detection method are as follows:

step 1: when testing the grout compactness of splice sleeve, the force transmission rod with the vibration sensor is extended into the wall body at the position of the grouting extraction hole or the grouting hole on the sleeve outer wall, to make the end of the force transmission rod securely fastened to the grouted body, and then fix the bottom of the preloading member to the wall surface;

step 2: rotate and tighten the force transmission rod through the nut which is fixed inside the device, so that the end of the force transmission rod is securely fastened on the grouted body of the splice sleeve structure to be tested, to ensure that the force transmission rod and grouted body will not separate during the test;

step 3: exert an impact to the end of the force transmission rod with a hammer, and acquire the variation curve of the vibration signal over time through the data acquisition system connected to the vibration sensor;

step 4: indoor full-scale model test was carried out, and set several groups of gradients grouted with different compactness for comparative tests; under the same hammering force condition as in Step 3, use the same dynamic detection device to determine the vibration signal of different grouted compactness with variation over time, and compared with the variation curve of the vibration signal measured in Step 3, to determine the actual distribution interval of grouted compactness, and the quantitative judgment of the grouted compactness of the splice sleeve is completed.

14. The detection method according to claim 13, wherein at the step 4, when performing the indoor full-scale model test, a total of 4 sets of different grout compactness gradients are set, namely grout-free, ⅓ grouted, ⅔ grouted, fully-grouted.

15. A method for detecting grout compactness of splice sleeve, wherein the method comprises the following steps:

S1: the rigid force transmission rod is securely fastened to the surface of rebar extended into the grouting extraction hole on the sleeve to be tested, and maintain a prestress between each other; the vibration sensor is fixed to the force transmission rod, which can synchronize with the vibration to acquire a data; a vibration sensor mentioned can be one or more combinations of a strain gauge, a displacement transducer, an accelerometer, a velocity transducer;

S2: exert a force along the axial direction of the force transmission rod to the rebar inside the sleeve structure, to make the rebar and the force transmission rod vibrate synchronously, and acquire the vibration signal of the force transmission rod under the pulse through the vibration sensor;

S3: obtain the parametric values of the indicators' characteristics from the vibration signal, and the indicators' characteristics is one or more combinations of the time-domain indicators or the frequency-domain indicators;

the time-domain indicators include: the amplitude of the $N^{th}$ half-wave in the waveform obtained from the time-domain vibration signal, N=1 or 2; the any width at any amplitude, and the peak-to-width ratio $R_{Npw}$ at any width at any amplitude $\Delta t_{Nwidth}$;

the frequency-domain indicator includes: the peak frequency which is corresponding to the maximum amplitude obtained from the frequency-domain vibration signal;

S4: according to the parametric values obtained in S3, based on the distribution interval of the indicators' characteristics parametric values corresponding to the compactness of different grouted body, determine the compactness of the grouted body in the splice sleeve to be tested.

16. The method for detecting grout compactness in the splice sleeve according to claim 15, wherein the half-wave can be a wave peak or a wave trough.

17. The method for detecting grout compactness in the splice sleeve according to claim 15, wherein the force transmission rod is supported perpendicular to the rebar inside the sleeve.

18. The method for detecting grout compactness in the splice sleeve according to claim 15, wherein the vibration sensor is one or more combinations of a strain gauge, a displacement transducer, a velocity transducer and an accelerometer.

19. The method for detecting grout compactness in the splice sleeve according to claim 18, wherein the vibration signal is the time-domain signal obtained after the electrical signal acquired by the strain gauge are amplified, filtered, and denoised.

20. The method for detecting grout compactness in the splice sleeve according to claim 19, wherein the filtering and denoising comprises of one or more combinations of a Wiener filter, a Kalman filter, a band-stop filter, and a low-pass filter.

21. The method for detecting grout compactness in the splice sleeve according to claim 15, wherein the vibration sensor is an accelerometer, the vibration signal is a velocity signal obtained by integrating the acceleration acquired by the accelerometer.

22. The method for detecting grout compactness in the splice sleeve according to claim 15, wherein the indicators' characteristics is adopting the peak-to-FWHM ratio of the $1^{st}$ half-wave in the waveform obtained from the time-domain vibration signal.

23. The method for detecting grout compactness in the splice sleeve according to claim 15, wherein the method for acquiring the time-domain indicators are:
after amplifying the electrical signal acquired by the vibration sensor, the filter removes the interference and noise to obtain the time-domain signal; from the $1^{st}$ half-wave waveform of the time-domain signal, one or more be time-domain indicators obtained comprises of the peak amplitude, FWHM (Full Width at Half Maximum) and peak-to-FWHM ratio.

24. The method for detecting grout compactness in the splice sleeve according to claim 23, wherein the filter is composed of a Wiener filter, a Kalman filter, a band-stop filter, and a low-pass filter; the amplified electrical signal is first subjected to Wiener filtering, and then to Kalman filtering get a smooth signal; next, input the signal into a band-stop filter to suppress the frequency of the powerline interference, after that filter out the high frequency through a low-pass filter at 3000 Hz.

25. The method for detecting grout compactness in the splice sleeve according to claim 15, wherein the method for acquiring the frequency-domain indicator are:
perform Fast Fourier Transform (FFT) on the time-domain vibration data to obtain the FFT power spectrum, and extract the frequency and amplitude from the power spectrum, and obtain the frequency and the corresponding maximum vibration amplitude from the frequency-domain graph, which is used as the frequency-domain indicator.

26. The method for detecting grout compactness in the splice sleeve according to claim 15, wherein the method for determining the threshold value of the indicators' characteristics parameters corresponding to the compactness of the different grouted bodies is as follows:
use the same model parameters of splice sleeve to be tested with different grout compactness, and obtain multiple sets of parameter values of indicators' characteristics for each grout compactness according to the method described in S1 to S3, the indicators' characteristics parametric values can be statistically analyzed to obtain the characteristic parameter threshold value interval corresponding to each of the grout compactness.

27. The method for detecting grout compactness in the splice sleeve according to claim 26, wherein the method for determining the threshold value of the indicators' characteristics parameters corresponding to the different grout compactness, the prestress exerted to the force transmission rod should be kept consistent at each test.

28. The method for detecting grout compactness in the splice sleeve structure according to claim 15, wherein multiple indicators' characteristics are used, the result of the grout compactness of splice sleeve to be tested needs to be determined according to each indicators' characteristics, and the results of the grout compactness of all the indicators' characteristics are synthesized to obtain the final results for grouted body compactness.

29. The method for detecting grout compactness in the splice sleeve according to claim 15, wherein the method for detecting grout compactness is performed after the grout in the sleeve is cured, and the curing time is preferably at least 24~48 h.

30. The method for detecting grout compactness in the splice sleeve according to claim 15, wherein the force transmission rod is inserted into the sleeve from the grouting extraction hole.

31. A method for detecting grout compactness in the splice sleeve according to claim 1, wherein the following steps are:
S1: install the rigid preloading member on the wall where the splice sleeve to be tested is located, fix the force transmission rod on the wall through the telescopic adjustment member; make the end of the force transmission rod securely fastened to the surface of the rebar in the sleeve, and maintain a prestress between each other;
S2: exert a force along the axial direction of the force transmission rod, to make the rebar and the force transmission rod vibrate synchronously, and acquire the original electrical signal sensed by the vibration sensor under the pulse; the original electrical signal is an analog signal and amplified by a small-signal/low-noise amplifier, and the electrical signal is sampled and converted into a digital signal by an analog-to-digital converter and stored in the data acquisition system;
S3: wiener filtering of the electrical signal and stored in the data acquisition system to enhance the target frequency;
S4: the electrical signal obtained after Wiener filtering is then inputted into the Kalman filter, and smooth filtering is performed according to steps S41 to S46, where:
S41: for the $i^{th}$ sampling point of $x_i$ in the amplified electrical signal value, a filter window of size $N_{fw}$ is set with the $i^{th}$ sampling point as the center, and a vector $Data_i$ composed of all sampling points in the filter window is obtained; the predicted state estimate of electrical signal value are $$\hat{Amp}^- = \bar{Data} = \frac{1}{N}\sum_{j=1}^{N} Data_i^j;$$

among them, Däta is the average of all sampling points in the current filter window, $Däta_i^j$ represents the signal's value of the $j^{th}$ sampling point in the vector $Data_i$, $j \in [1, N_{fw}]$;
S42: covariance matrix of the observation noise $$R = \frac{1}{N-1}\sum_{j=1}^{N_{fw}} |Data_i^j - Däta|^2;$$

S43: calculate optimal Kalman gain $$K = \frac{|\hat{Amp}^-| \cdot H^T}{H \cdot |\hat{Amp}^-| \cdot H^T + R},;$$

among them,
H is the observation matrices, T means transpose;
S44: calculate the amplitude of the output's electrical signal value after filtering at the $i^{th}$ sampling point:

$$\hat{Amp} = \begin{cases} -\{|\hat{Amp}^-| + K \cdot (|Data_{x_i}| - H \cdot |\hat{Amp}^-|)\}, & \hat{Amp}^- < 0 \text{ and } Data_{x_i} < 0 \\ |\hat{Amp}^-| + K \cdot (Data_{x_i} - H \cdot \hat{Amp}^-), & \text{others} \end{cases}$$

In the formula: $Data_{x_i}$ represents the sampling value of the $i^{th}$ sampling point $x_i$;

S45: before filtering the next sampling point, update the predicted state estimate of electrical signal value $\hat{Amp}^- = (1-K \cdot H) \cdot D\ddot{a}ta+Q$, where Q is the state transition covariance matrix; meanwhile, $i=i+1$;

S46: repeat the steps S42 to S45 for the remaining sampling points in the amplified electrical signal value in sequence to complete Kalman filtering;

S5: digital filtering of the Kalman-filtered signal data; The process is to input the signal into a band-stop filter to suppress the frequency of the powerline interference, and then filter out the high frequency through a low-pass filter at 3000 Hz, and derive a new time-domain data;

S6: the amplitude of the $N^{th}$ half-wave in the waveform curve obtained from the time-domain vibration signal; the any width at any of amplitude, and the peak-to-width ratio at any width at any amplitude; where N=1 or 2;

S7: perform FFT on the new time-domain data to obtain the FFT power spectrum, and extract the frequency and amplitude in the power spectrum, and obtain the peak frequency; the peak frequency is a frequency corresponding to the maximum power amplitude in the frequency-domain;

S8: taking any one or more of the peak amplitudes, the pulse width, the peak-to-width ratio, and the peak frequency as the indicators' characteristics; According to the parametric values obtained from S6 to S7, based on the distribution interval of the indicators' characteristics parametric values corresponding to the compactness of different grouted body, determine the grout compactness of the splice sleeve to be tested.

32. The method for detecting grout compactness in the splice sleeve according to claim 31, wherein the indicators' characteristics is preferably the peak-to-FWHM ratio of the $1^{st}$ half-wave in the waveform obtained from the time-domain vibration signal.

* * * * *